(12) United States Patent
Gardiner et al.

(10) Patent No.: US 6,886,964 B2
(45) Date of Patent: May 3, 2005

(54) ILLUMINATOR WITH FILTER ARRAY AND BANDWIDTH CONTROLLER

(76) Inventors: Allan Gardiner, 65 Franciscan Way, Kensington, CA (US) 94707; Constance Haber, One Monroeville Center #150, Monroeville, PA (US) 15146

(*) Notice: Subject to any disclaimer, the term of this patent is extended or adjusted under 35 U.S.C. 154(b) by 296 days.

(21) Appl. No.: 10/180,643

(22) Filed: Jun. 26, 2002

(65) Prior Publication Data

US 2003/0035301 A1 Feb. 20, 2003

Related U.S. Application Data

(60) Provisional application No. 60/301,376, filed on Jun. 26, 2001, and provisional application No. 60/301,319, filed on Jun. 26, 2001.

(51) Int. Cl.[7] .................................................. F21V 9/10
(52) U.S. Cl. .................... 362/276; 362/293; 362/583
(58) Field of Search ............................. 362/1, 2, 3, 16, 362/17, 18, 268, 277, 278, 279, 282, 290, 293, 310, 311, 317, 351, 354, 276, 551, 552, 554, 555, 572, 583; 607/80, 88, 90, 93

(56) References Cited

U.S. PATENT DOCUMENTS

| | | | | |
|---|---|---|---|---|
| 624,392 A | * | 5/1899 | Smith | 362/572 |
| 1,525,541 A | * | 2/1925 | Hall | 362/290 |
| 1,965,865 A | * | 7/1934 | Thompson | 607/93 |
| 2,227,422 A | * | 1/1941 | Boerstler | 607/93 |
| 3,437,803 A | * | 4/1969 | Schafer et al. | 362/572 |
| 3,930,149 A | * | 12/1975 | French | 362/293 |
| 4,101,957 A | * | 7/1978 | Chang | 362/293 |
| 4,240,133 A | * | 12/1980 | Haina et al. | 362/293 |
| 4,281,366 A | * | 7/1981 | Wurster et al. | 362/572 |
| 4,519,020 A | * | 5/1985 | Little | 362/268 |
| 4,535,394 A | * | 8/1985 | Dugre | 362/293 |
| 4,745,531 A | * | 5/1988 | Leclercq | 362/293 |
| 4,989,604 A | | 2/1991 | Fang | 128/421 |
| 5,031,078 A | * | 7/1991 | Bornhorst | 362/552 |
| 5,265,598 A | * | 11/1993 | Searfoss et al. | 607/88 |
| 5,269,746 A | | 12/1993 | Jacobson | 600/13 |
| 5,344,384 A | | 9/1994 | Ostrow et al. | 600/13 |
| 5,405,369 A | | 4/1995 | Selman et al. | 607/88 |
| 5,441,531 A | * | 8/1995 | Zarate et al. | 607/90 |
| 5,800,479 A | | 9/1998 | Thiberg | 607/88 |
| 5,814,078 A | | 9/1998 | Zhou et al. | 607/1 |
| 6,140,346 A | | 10/2000 | Andrulis, Jr. et al. | 514/323 |
| 6,238,425 B1 | | 5/2001 | Thiberg | 607/88 |

\* cited by examiner

*Primary Examiner*—John Anthony Ward
*Assistant Examiner*—Ismael Negron
(74) *Attorney, Agent, or Firm*—Fliesler & Meyer LLP

(57) ABSTRACT

Illuminators and systems that permit the production of a beam of electromagnetic radiation having selected peak wavelength, bandwidth, intensity, pulse frequency and pulse duration for a variety of analytical and therapeutic applications. Multiple beam illuminators use filter elements arranged into filter arrays, having characteristic wavelength absorption properties. By providing a series of filter arrays formed into tracks having defined wavelength offsets, radiation passing through a portion of a track can be modified to include selected peak wavelength and bandwidth. Selection of peak wavelength(s) and bandwidth can be accomplished using mechanical interrupters, mechanical shutters, or electro-optical devices including liquid crystal device. Multiple output beams permit the coordinated illumination of a target, and sensors provide feedback regarding the effects of illumination on a target. Computer storage devices, programs, and controllers can provide easy selection of the characteristics of the output beams. Output beams can have a variety of different shapes and configuration.

22 Claims, 21 Drawing Sheets

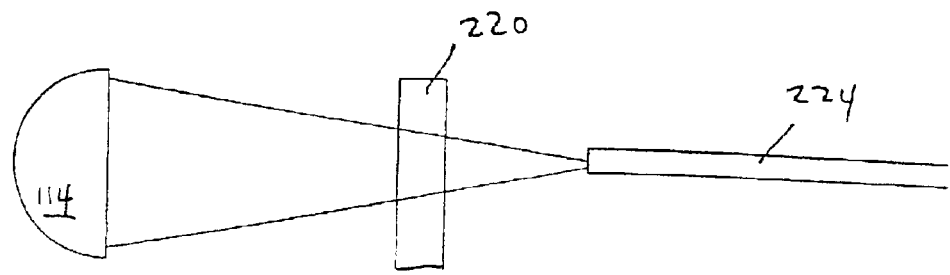
FIGURE 3a
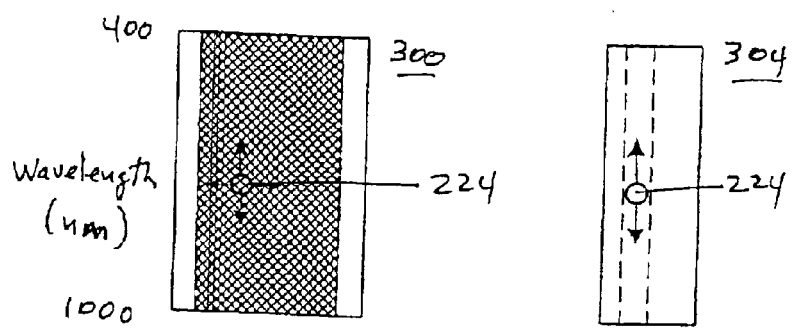 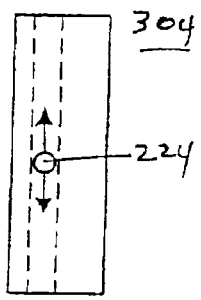
FIGURE 3b    FIGURE 3c

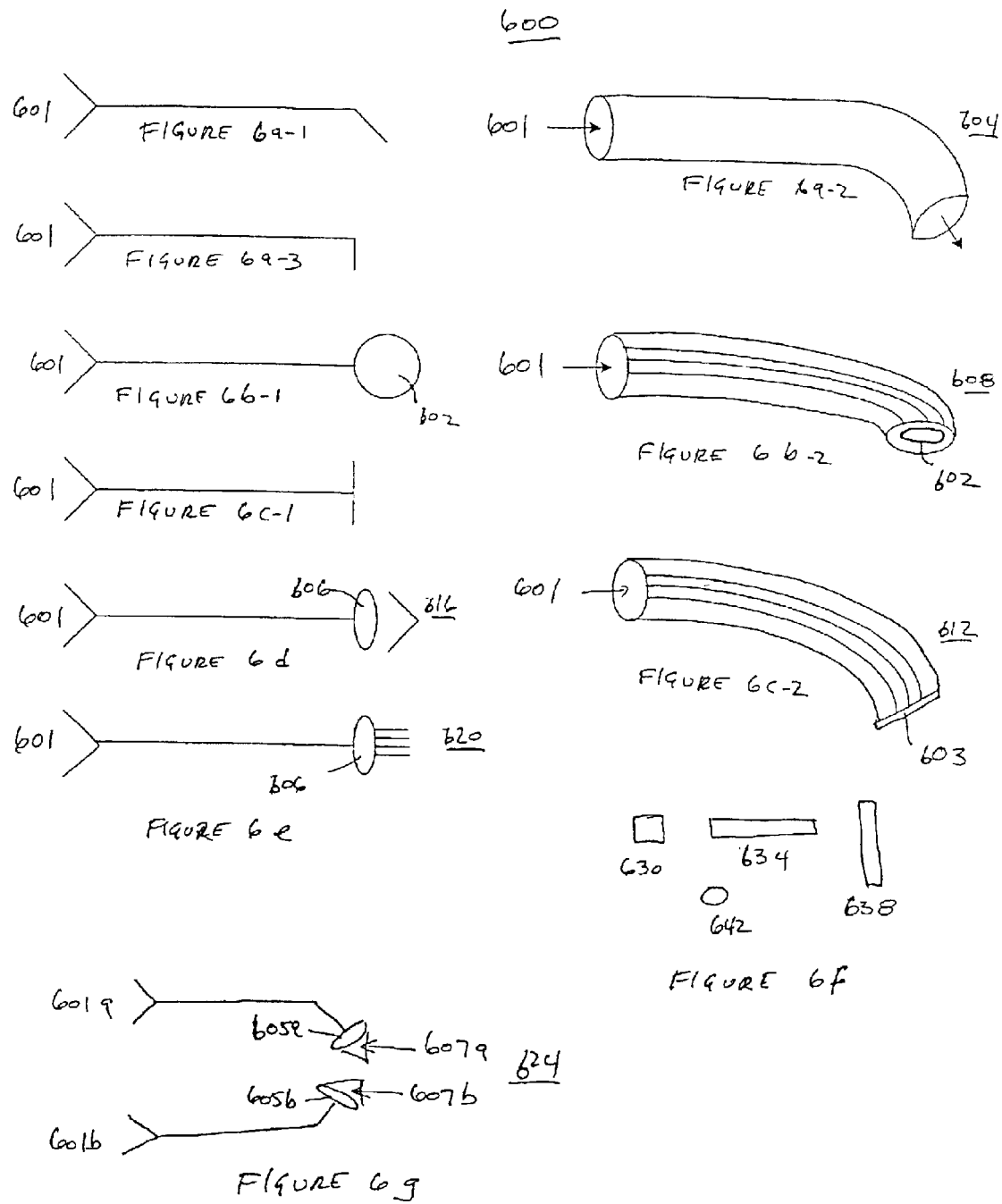

ILLUMINATOR WITH FILTER ARRAY AND BANDWIDTH CONTROLLER

RELATED APPLICATIONS

This U.S. Utility Patent Application claims priority to U.S. Provisional Patent Application, Ser. No. 60/301,376, entitled "Multiple Wavelength Illuminator," filed Jun. 26, 2001, and U.S. Provisional Patent Application Ser. No. 60/301,319, entitled "Therapeutic Methods Using Electromagnetic Radiation," filed Jun. 26, 2001.

This U.S. Utility Patent Application is related to U.S. Utility Patent Application Ser. No. 10/180,802, entitled "Therapeutic Methods Using Electromagnetic Radiation," Allan Gardiner and Constance Haber, inventors, filed Jun. 26, 2002. Each of the above applications is incorporated herein by reference.

BACKGROUND

1. Field of the Invention

This invention relates to devices used for illumination of target objects by electromagnetic radiation. In particular, this invention relates to illumination devices having multiple beams, each of which can have selected wavelength, bandwidth, pulse duration, pulse frequency and intensity.

2. Description of Related Art

Physical treatment of disorders associated with the peripheral nervous system is becoming increasingly important in the management of disease. Acupuncture, acupressure and related healing arts typically involve the mechanical stimulation of peripheral sensory and motor nerves. In acupuncture, needles are typically inserted through the skin to reach the desired locations. Acupressure involves the application of localized surface pressure above the desired site and the transmission of that pressure to the nerves under the skin.

Stimulation of peripheral nerves can be accomplished using heat or infrared radiation. Infrared radiation can be produced using lasers or sources of incoherent electromagnetic radiation.

There is a need in numerous technologies for providing two or more selectable wavelengths of radiation. Examples include electromagnetic radiation therapy, fluorescence microscopy, contrast enhancement for photography or machine vision, and simulation of radiation combination effect from sources of radiation having narrow spectral ranges, such as light emitting diodes ("LEDs"), and characterization of the quality of optical systems.

There is also a need in the art for inexpensive devices that can produce electromagnetic radiation of discrete wavelengths and deliver beams of those discrete wavelengths separately from one another.

A variable bandpass tunable filter system is available commercially from Ocean Optics, Inc. that consists of two filters, each coated with a linearly variable multilayer interference coating, providing a "wedge" filter. To select a bandwidth, two filters are placed overlapping each other, in series with the source of radiation, so that a beam of radiation passes through both filters. To increase the bandwidth of output radiation, the two filters are offset relative to each other. Although this system can provide output variable bandwidth, because the output radiation must pass through both filters, desired wavelengths the output beam will be reduced in intensity.

Therefore, there is need in the art for inexpensive illuminators that can provide output beams of electromagnetic radiation having controllable wavelength, bandwidth and intensity.

SUMMARY OF THE INVENTION

One object of this invention is the production of devices for illuminating target objects with electromagnetic radiation in selected wavelengths in the range from ultraviolet to infrared.

Another object of this invention is the manufacture of devices that can provide multiple beams of electromagnetic radiation of controlled wavelength ranges.

Yet another object of this invention is the manufacture of devices that can be used to direct separately controlled beams of electromagnetic radiation to selected target sites.

A further object of this invention is the manufacture of devices that can produce electromagnetic radiation having controllable ranges of wavelengths.

Yet another object of this invention is the manufacture of devices that can produce electromagnetic radiation having controllable bandwidths.

An additional object of this invention is the production of systems for therapeutic use of electromagnetic radiation that can incorporate illuminators for delivery of electromagnetic radiation, monitoring effects of therapeutic radiation, for coordinating therapeutic intervention and subject's physiological responses to therapy, and devices for maintaining information concerning electromagnetic radiation therapy of individual subjects and groups of subjects.

These and other objects are achieved by devices that in certain aspects, incorporate a generator of non-coherent electromagnetic radiation ("illumination source"), band pass filters ("filters"), and waveguides (including optical fibers). An illumination source can produce a broad range of wavelengths of electromagnetic radiation, including, but not limited to ultraviolet, visible and infrared wavelengths. The term "illumination source" includes embodiments having a single source of radiation and one or more devices for dividing the radiating element ("beam splitter"). Desired wavelengths can be selected by electromagnetic filtering devices which selectively absorb undesired wavelengths. The radiation passing through the filter can then be captured by one or more waveguides for transmission to sites remote from the source. A portion of the radiation produced by the source may be captured into a focusing device for filtering and transmission to therapeutic sites. A beam splitter or separate sources can two or more separate beams of electromagnetic radiation, which can be separately controlled.

Selection of a peak wavelength in a beam can be accomplished by using a plurality of "filter arrays," each array comprising a plurality of filter elements, each filter element having selected transmission characteristics. Materials having known transmission spectra are known in the art. By selecting materials having desired transmission spectra, one can produce a series of filters having different transmission characteristics. For some filter materials, the radiation transmitted through the filter material does not necessarily represented as a single wavelength, but rather comprises radiation having multiple wavelengths, all of which comprise the "bandwidth" of the beam of radiation. Each of these materials has characteristic maximum transmitted wavelength ("peak wavelength" or "peak λ") and bandwidth dispersion ("bandwidth"). Bandwidth means the range of wavelengths in a beam that are either greater than or less than the peak wavelength.

By way of illustration only, one filter can remove wavelengths outside the "orange" range, permitting only wavelengths in the orange visible range to pass. Next to the "orange" filter, a "yellow" filter may be present that removes wavelengths outside the yellow region. When the beam of radiation passes through the "orange" filter, orange radiation is produced, and when the beam passes through the "yellow" filter, yellow radiation is produced. By placing the filters in non-overlapping fashion, in parallel with each other, one portion of the beam passes through the "orange" filter, and another portion of the beam passes through the "yellow" filter. After combining the outputs of the two filters, the resultant radiation has characteristics of both the "orange" and the "yellow" filters. This arrangement can minimize undesirable losses of intensity that can occur when an output beam passes through overlapping filters.

By providing a plurality of filters, each having different bandwidth characteristics in an array, and by moving the filters relative to the source beam, one can control the wavelengths and the bandwidth dispersion produced by the device. Thus, it can be desirable to provide an array having a large number of different filters arranged progressively, with filters having short maximum transmitted wavelength at one end of the array and filters having long maximum transmitted wavelengths at another end of the array. By moving the filters relative to the source beam, or by moving the source beam relative to the filters, the wavelength of an output beam can be controlled. In embodiments using linear filters, movement of the series can be accomplished using linear motors and the like. A filter array can alternatively be arranged in a circle or arc on a disk. Angular (rotational) movement of the filter array relative to an incident beam of radiation can be accomplished using rotary means, such as a rotary motor. Radial movement can be accomplished using, for example, a linear motor.

Controlling the bandwidth of radiation can be accomplished using series of filter arrays described above. For example, to produce radiation having a desired mean wavelength (e.g., and "orange" color) and a narrow bandwidth, a single "orange" filter can be used. The bandwidth can be determined by the bandwidth characteristics of the filter medium. To produce radiation having the same mean "orange" wavelength as above, but having a greater bandwidth dispersion, one can use a plurality (e.g., two or more) similar filter arrays, having, for example, "red", "orange" and "yellow" regions near each other. If the "orange" regions are adjacent to each other, and a portion of the beam passes through only the "orange" regions of the filter arrays, the output will be "orange" and will have a relatively narrow wavelength bandwidth. However, if the "orange" region of one filter is offset, so as to be adjacent to the "red" region of one and the "yellow" region of yet another filter array, then different portions of the source beam can be directed to pass through each filter. After combining the three separate output beams into a single beam (e.g., using a "mixer"), the transmitted radiation comprises all three "colors". In this case, the maximum transmitted wavelength can be orange, yet both red and yellow wavelengths can also be present. The previous discussion is intended only to provide an example of the principle of operation of the devices of this invention, and is not intended to be limiting. Numerous other configurations of filters, filters having certain maximum transmitted wavelengths and bandwidth dispersion characteristics are possible, and are all included in this invention. Other configurations include those that can be used to select wavelength and bandwidth characteristics in the ultraviolet, red, blue, green, infrared and other, desired regions of the electromagnetic spectrum.

In other aspects of this invention, bandwidth can be controlled by adjusting the dimensions of an aperture that selects a portion of the output beam containing desired spectra. Thus, with apertures having dimensions comparable to a single filter element in a filter array, the transmitted bandwidth will be small. In contrast, if an aperture is large and encompasses a plurality of filter elements, the transmitted radiation can have a wider bandwidth.

In addition to providing a fixed, single wavelength, the wavelengths of electromagnetic radiation can be varied during application. For example, in some embodiments, it can be desirable to provide "wavelength variations" around a "central wavelength." In such embodiments, a central wavelength can be selected and the illuminator can be used to vary the wavelength to include wavelengths of longer or shorter wavelengths, typically in the range of about ±1 nm to about ±100 nm, alternatively about ±5 nm to about ±50 nm, in other embodiments in the range of about ±20 nm to about ±50 nm. It can be appreciated that other ranges of wavelength variation can be used. It can also be appreciated that one can have variations about a central wavelength that are asymmetrical, that is, the change in wavelength can be greater in one direction than in the other.

Similarly, the rate of change of wavelength, from the lowest to the highest can be in the range of about 1 sec to about 100 sec., alternatively about 5 sec to about 50 sec, in other embodiments in the range of about 20 sec to about 50 sec. Additionally, the rate of change of wavelength can be in the range of about 1 nm/sec to about 100 nm/sec, alternatively in the range of about 5 nm/sec to about 50 nm/sec, and in other embodiments, from about 20 nm/sec to about 50 nm/sec.

Moreover, the rate of change of wavelength can be varied, and includes by way of example only, linear changes, a sinusoidal output, whereby the rate of change of wavelength varies according to a sine wave function, in other embodiments, the change of wavelength can be trapezoidal. It can be appreciated that any type of a large number of variations in wavelength about a central wavelength can be used.

To create wavelength variations as described above, in certain embodiments of this invention, a series of filters can be provided that, when placed in a beam of electromagnetic radiation, produces an output beam having a spatially arranged series of different wavelengths (e.g., red at one end and blue at another end). Thus, by placing interrupters in front of the output beam and by changing the relative positions of the output beam and the interrupter, one can select various portions of the output spectrum. For example, using a linear array of filters having different wavelengths represented in a two-dimensional array, a circular interrupter that has a "window" or transparent region that encompasses different distances from an axis of rotation (e.g., a "eccentric aperture") can be used to select different portions of the filter array and thereby select wavelengths that can vary over time. It can be appreciated that the input beam can encompass a relatively large portion of the interrupter window.

Additional aspects of this invention include the use of arrays of shutters positioned relative to a filter array so that radiation passing through each filter element can be blocked by an individual shutter. Shutters can be controllable either by mechanical means (e.g., rotating mirrors or plate shutters, or electrical means (such as liquid crystal devices or other electro-optical shutters). By selectively opening desired shutters, radiation passing through a desired part of a filter array can be captured by a waveguide or series of waveguides. In such fashions one can provide output beams having desired intensity, desired peak wavelength and desired bandwidth.

By directing the output, of such an array, two or more discrete, separate beams can be provided.

Waveguides can be flexible, so that the output of the waveguides can be directed toward desired target locations.

This invention includes devices that regulate the intensity of radiation. Such devices can vary the intensity of the source of radiation, the use of shutters, apertures and the like, and by the use of interrupters that interrupt the beam for certain periods of time during a duty cycle.

One or more "interrupters" or "choppers" can interrupt the output beam to provide repeated pulses of radiation, the pulses having desired frequency and each pulse having a desired duration. Interrupters can also be used to alter the total amount or dose of radiation delivered. Other electronically operated interrupters or mirrors maybe used to modulate the intensity of the output beam. Some common types of electronic interrupters include "liquid crystal devices", or "LCD"s.

The shape of an output beam can be controlled so as to produce beams having circular, annular, polygonal, or other desired shape.

Additional components of systems of this invention include computer interface, software and hardware for running programs that control the output beams and record information obtained from monitoring sensors. Systems of this invention can also include memory devices and software that maintain records of treatment protocols, physiological responses to treatment, efficacy of therapy, annotations, other information regarding the subject's therapy and condition, and can include transmission of subject information to and from remote sites.

Systems including the illuminators of this invention can be used to treat acute and chronic pain, and a variety of disorders involving abnormalities in the function of excitable tissues, including, but not limited to peripheral somatic nerves, autonomic nerves, muscles, connective tissues and the central nervous system. Additional description of therapeutic uses are included in concurrently filed patent application titled "Therapeutic Methods Using Electromagnetic Radiation" Constance Haber and Allan Gardiner, inventors, incorporated herein fully by reference.

BRIEF DESCRIPTION OF THE FIGURES

This invention will be described according to embodiments thereof. Other features of the embodiments of this invention are described in the Figures, in which:

FIGS. 3a–3i depict embodiments of this invention having rectangular filter arrays.

FIGS. 6a–6g depict common types of end effectors used with the illuminators of this invention.

DETAILED DESCRIPTION OF THE INVENTION

Figure 1:
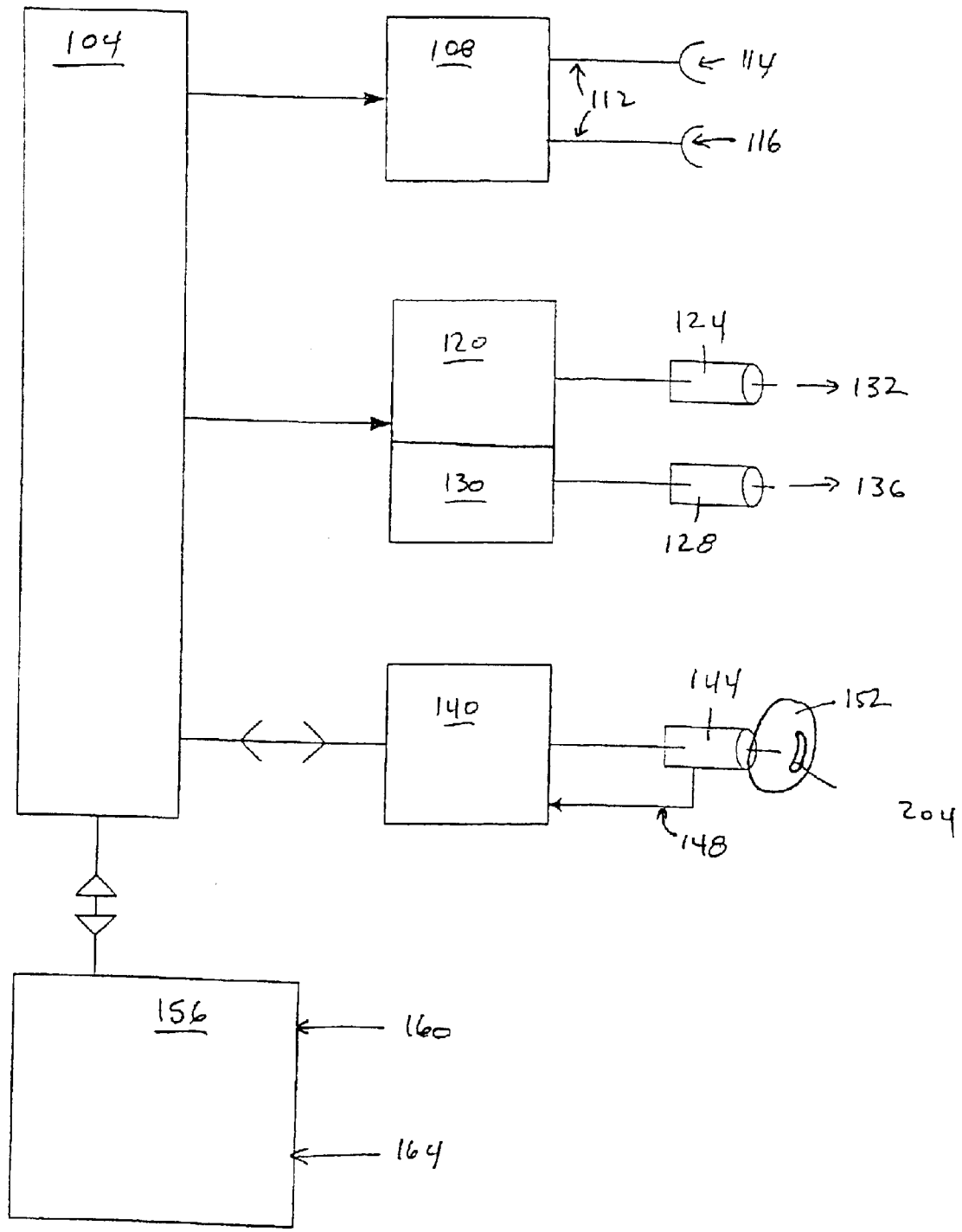
FIG. 1 depicts a schematic diagram of a system of this invention for producing electromagnetic radiation.

Illuminators of this invention include sources of electromagnetic radiation (including visible radiation "light") that incorporate simple, reliable means for producing beams of radiation having desired wavelengths and/or other characteristics. A source of broad-band electromagnetic radiation produces radiation having a wide range of wavelengths, including those desired. One or more filters placed in the path of the radiation can attenuate certain wavelengths that are not desired, permitting desired wavelengths to pass through the filter and directed to a target. The wavelengths of radiation that pass through the attenuator ("filter") have a characteristic spectrum, depending upon the properties of the attenuator. It can be desirable to rapidly change the wavelength, wavelength bandwidth characteristics, polarization, to provide pulses of radiation, and to direct beams of radiation to a desired, localized target area. Means are provided to supply radiation, to attenuate radiation, to direct and shape a beam of radiation, and provide a pulsatile beam having desired pulse duration and frequency to suit a particular purpose. Systems are provided to coordinate the production of one or more beams of radiation and to direct beams independently of one another. In some of these embodiments, the characteristics of multiple beams of electromagnetic radiation can be regulated separately.

Radiation can be used to treat pathophysiological conditions, such as those caused by diseases or disorders. Physiological responses to electromagnetic radiation of different frequencies is variable. For example, ultraviolet radiation of wavelengths in the range of about 200 nanometers ("nm") to 300 nm (ultraviolet wavelengths) can be used for sterilizing wounds or other physical objects, and infrared radiation of wavelengths longer than 700 nm maybe used to heat tissues. Each wavelength of the spectrum from 200 nm to about 1000 nm or more can be absorbed by tissues differently to provide different responses. Simultaneous application of two or more wavelengths can be used to augment the response that would have been effected by application of a single wavelength. Because of the variability of each subject (animals and human), the ability to select specific wavelengths for that individual is desirable. Additionally, varying the wavelength during treatment can augment therapeutic effects.

A Illuminator Radiation sources

Illuminators of this invention are not dependent upon any particular radiation source for operation. Each type of source (e.g. tungsten, tungsten-halogen, arc, gas discharge, broad spectrum radiation emitting devices "LEDs", and the like) has a spectral output that may be useful for various applications. In certain emdodiments, incandescent lamps can provide desirable ranges of wavelengths, can be found in a variety of configurations, can be inexpensive and readily available. In other embodiments, for example, arc lamps provide radiation containing wavelengths from ultraviolet through infrared that can be used as a radiation source that can be used to deliver beams of electromagnetic radiation having a narrow bandwidth that can be selected over a wide range of peak wavelengths. Another series of embodiments include gas discharge lamps that can supply radiation pulses having high power. Some lamps, such as commercial tungsten-halogen reflector lamps are pre-focused such that it can be possible to reduce the number of lenses are required in the optical radiation path to provide a beam having desired dimensions.

B Filter Based Selection of Wavelength and Bandwidth Characteristics

Certain embodiments of this invention include means for controlling the output of electromagnetic radiation arising from a lamp. In several embodiments of this invention, the means for controlling the output comprises an attenuator, dichroic filter or series of attenuators or dichroic filters. As used herein, the term "dichroic" means a filter or attenuator that passes certain wavelengths of radiation based upon the wavelength of that radiation.

A plurality of filters can be used to adjust the bandwidth of the output radiation beam. In certain embodiments, a filter assembly comprises a series of individual filter elements, each having a transmission maximum at a certain wavelength. This wavelength is termed the "peak", "central", or "mode" wavelength. Additionally, each filter element has a certain range of wavelengths that can pass through in sufficient amount to be useful for the intended purpose of the illuminator. The wavelengths that can pass through a filter element is termed the "bandwidth" or "wavelength range". For certain filter elements, the bandwidth can be relatively narrow, that is, the peak wavelength and only a relatively narrow range of wavelengths on either side of the peak can pass through in significant amounts. In contrast, for other filter elements, the intrinsic absorptivity of the filter material is such that a relatively wide range of wavelengths can pass through in significant amounts. Such filters are herein termed "wide bandwidth" filters.

Many types of filters are available, and any type of filter material can be used that is compatible with the types of electromagnetic radiation, the other components of the system, and the ultimate use of the illuminators. For example, plastic, glass, quartz, resin or gel filters can be provided in sizes that can be adapted for use in a variety of configurations. In certain embodiments, filter elements can be made of a base material and then provided ("doped") with a material suitable for controlling the radiation emitted from the illuminator. In other embodiments, coated glass can be used.

Once manufactured, a plurality of filter elements can be arranged in an array. For example, a series of filters can be arranged linearly, to provide a series of filters having progressively increasing (or decreasing) peak transmission wavelengths. Alternatively, a linear array of filters can be provided in which certain peak wavelengths are clustered, that is, not necessarily in progressively increasing (or decreasing) peak transmission. In certain other embodiments, filter elements can be arranged in a circular or ovoid fashion on a rotating disk. Thus, when the disk rotates and/or translates relative to a radiation source, the bandwidth characteristics of the radiation can be selected. Alternative embodiments of this invention utilize a series of fixed filters which allows selection of spectral transmission based upon the location of the filter assembly relative to the beam of radiation passing through. Alternatively, a single filter can be manufactured that has bandwidth characteristics controlled by way of example, an externally applied electrical field.

Regulation of the peak wavelength can be readily accomplished using dichroic filters. Filters having selected peak wavelength bandpass characteristics are known in the art, and can be obtained, for example from Ocean Optics, Inc. Filters can be made using precision lithography, such as used in the semiconductor manufacturing industry.

The "bandwidth" of a filter assembly is the range of frequencies (wavelengths) that pass through a filter. A band pass filter has a transmission that is high for a particular band of frequencies and with a lower transmission of frequencies above and below this band. The width or narrowness of the band for frequencies transmitted through a filter is often measured by the "half bandwidth" that is the full width of the band at half-power or half of the peak transmittance points specified in either wavelength units or in percent of center wavelength. Another common measure of a bandwidth filter is the "half-power point" that is the wavelength at which a filter is transmitting one-half of its peak transmission power. For example, for a bandwidth filter with a peak transmission of 80 percent, the wavelengths at which it transmits 40 percent are the half-power points.

Color is an attribute of visual experience that can be described as having quantitatively specifiable dimensions of hue, saturation, and brightness or lightness. The visual experience also can include other aspects of perception, including extent (e.g. size, shape, texture, and the like) and duration (e.g. movement, flicker, pulse duration, and the like). Color names (e.g. blue, turquoise, etc.) are often used to describe various wavelengths or groups wavelengths of visible light. The radiation used in scientific, industrial, and medical instruments is generally specified by the wavelengths transmitted and the proportions of each wavelength within the active area. The use of color names can be a convenient way to express the appearance of the light. For purposes of these descriptions, color names can be used to convey an approximate range of wavelengths used. Color names often describe combinations of wavelengths of radiation from differing portions of the visible spectrum. The color to wavelength conversion identity varies slightly from the various resources. One source, Van Nostrand's Scientific Encyclopedia, Third Edition, lists the conversion as:

| Violet | 390–455 nm |
| Blue | 455–492 nm |
| Green | 492–577 nm |
| Yellow | 577–597 nm |
| Orange | 597–622 nm |
| Red | 622–770 nm |

However, other reference books recite other wavelength ranges for the above colors. Thus, we do not intend that each color name be provided with an exact wavelength or bandwidth characteristic. Rather, each of the colors described herein is intended to be a guide for use of the devices of this invention. For example, for therapeutic purposes, the color "violet" may contain amounts of longer, blue wavelengths, and may also include certain amounts of shorter wavelengths, in the ultraviolet range. Similarly, the color yellow may contain certain amounts of green and/or orange light. Moreover, other colors described by their common names may include greater or lesser amounts of other, wavelengths.

Some commonly named colors include two or more wavelength bands of light. Magenta, for example, has two peaks, one in the violet region and another in the red region. Purple has peaks similar in wavelength to Magenta but has higher violet transmission.

Perception of a given color may result from combinations of wavelengths added together. The most common combination is red+green+blue. These three colors are used in differing proportions in computer monitors and displays to create the colors available on the display. Other combinations of filters maybe used in parallel to produce perceived color. The printing industry adapts to varying ink properties as a routine matter.

1. Filters

When used for therapeutic purposes, a purpose of filtering radiation to specific narrow bandwidth characteristics is to provide radiation having wavelengths that interact with particular biologic components (e.g. nerves, muscles, blood vessels, blood, etc), specific chemicals or molecules, or other wavelength-specific receptors. By selecting the desired wavelength(s) and the bandwidths of wavelengths can permit a rapid and efficient means of delivering a reproducible electromagnetic stimulus to an area or volume of tissue or other material.

In certain embodiments, our invention utilizes filters that transmit a single wavelength or narrow bandwidth of wavelengths. One aspect of our filter design permits control of the width of the bandwidth by means of moving the filter in two directions with respect to the radiation path. Movement of the filter relative to the radiation source in one direction controls the peak, center, mean or mode wavelength, and movement in another direction can provide radiation having differing bandwidth ranges.

In certain embodiments, a fixed aperture that limits the transmission of radiation to a well-defined area such that the mix of wavelengths transmitted represents the sum of filter elements within that aperture. The amount of radiation at the peak transmission wavelength may diminish as additional filter elements of differing wavelengths are introduced into the radiation path. This design is simple and can use any desired aperture area practical. Movement of the filter during treatment allows a continuously variable peak wavelength, providing a "wavelength variation," which can be varied in magnitude (e.g., how much the wavelength changes around a central wavelength), intensity, pattern of wavelength change and speed of wavelength change.

2. Linear Filter Arrays

In certain embodiments, a series of filters having different fixed transmission characteristics may be placed between a radiation source and one of the waveguides. These filters may be used to select the desired ranged of wavelengths or to exclude large segments of the spectrum, such as, for example, infrared blocking filters.

In other embodiments of this invention, a linear filter, such as a Schott Veril 60, may be manufactured such that the transmission spectrum continuously changes with respect to the position along the filter array. The variable spectrum characteristics of the filter array are accessed as desired by moving the filter array along the variable wavelength axis through the radiation beam in the illuminator section by means of a mechanism. The mechanism must allow repeatable motion when driven manually or by a motor. One embodiment of this apparatus uses a leadscrew and carriage assembly to move the filter. A linear version of the circular variable filter described below may be manufactured as either an array of individual filters or as an array that permits changes in the width of the spectrum and maximum transmitted wavelength by moving the filter array in two axes transverse to the radiation beam.

It other embodiments, "wedge" type filters can be used, in which an absorptive medium is provided on a substrate. One portion of the wedge typically has a thinner layer of absorptive medium, and another portion typically has a thicker layer of absorptive medium. An interference pattern can be generated by wavelengths of radiation, so that radiation transmitted can have different wavelengths, depending upon the thickness of the layer of absorptive material. Certain filters useful for the devices of this invention can be obtained commercially from Ocean Optics, Inc. Thus, in certain embodiments, two or more wedge filters can be place near one another so that the radiation emitted by both filters can be collected and used. However, the above description is not intended to be limiting, rather any available filter types can be used.

In certain embodiments, arrays of small filter elements can be provided that have small size (about 1 $\mu$m on a side) and manufactured using photolithographic methods, as used in the semiconductor manufacturing industry. For radiation having short wavelengths, (e.g., 200 nm), the size of the filter elements can be even smaller (e.g., 200 nm). Planar arrays of such filters can have large numbers of individually manufactured filters, and, if desired, each can have different bandpass characteristics. Certain of these types of filter arrays can be obtained from Ocean Optics, Inc.

Filters may be fixed in place or moved into or out of the beam by mechanisms provided for that purpose. The characteristics of the filters are selected for the requirement of the system. For example, a filter may pass two or more fixed wavelengths of radiation through one illumination section which is then combined with a variable wavelength radiation from another illumination section to provide more specific narrow wavelengths than the number of illumination sections. Additional filters may be selected or automatically placed in the radiation path as designed into the particular mechanism. Some example of the filter types are narrow band, cut-off, or bandwidth filters.

The variable filter used to select the wavelength or spectrum of wavelengths for each illumination section may be created by a variety of methods and physical shapes and sizes. The filter media may be of any type that has the desired radiation transmission characteristics. Some example filters include gel filters, interference filters, dichroic filters, substrate filters or other types known in the art. The geometry of the illumination beam and the shape and position of filters can be adjusted to obtain radiation having desired spectral characteristics.

3. Circular Filter Arrays

In certain embodiments, a circular filter array can be used that has a pattern of filter elements or materials that allow transmission of different wavelengths at different rotational positions around the circular filter array. The filter array may be rotated to discrete angular positions manually or motorized for remote control. A means of repeatedly returning to a desired angular position can be provided by a dial or by a memory element associated with the motorizing system. Some examples of a motorizing system are a stepping motor with a means of initializing the angular position, or, a servo motor with an encoder which provides initializing information.

The dimensions of the beam of radiation relative to the active circumference of the illumination section can contribute to the spectral distribution of the radiation entering the waveguide. In some embodiments, a variable filter pattern can comprise an annulus that has variable wavelength transmission along the circumference that passes through the illumination path as the filter is rotated about its axis of rotation. One result can be that each angular position corresponds to a different specific narrow spectrum of wavelengths. For filter arrays having continuous and monotonically changing transmission along the circumference of the array, the width of the radiation spectrum emerging from the illumination section is determined by the ratio of the active circumference to the diameter, or width (for non-circular entrance ports) of the beam entering the waveguide. A filter array may also be manufactured that comprises a series of discrete filter elements or materials which are accessed by rotation of the filter disk.

In certain embodiments, a process permits manufacturing of a pattern such that the transmission characteristics of any angular and radial position can be selected. The pattern may be such that the area of each pattern element is small relative to the active area of the beam. This allows the center of rotation of the circular filter to be moved relative to the beam to provide differing transmission characteristics based on both active radius and angular position. For example, the outer radius portion of the pattern area may have a constant linear variability, for example, from 400 nanometers ("nm") to 1000 nm, that provides a narrow spectrum of wavelengths to emerge from the illumination section, while the inner portion of the pattern area may provide a mixture of elements that combine to provide a broader spectrum of wavelengths to emerge from the illumination section. Thus moving the center of rotation and angle of the filter relative to the radiation beam can select a specific narrow wavelength or a wider spectrum of wavelengths. This ability to select center wavelength and spread of wavelengths allows the system to provide additional control over the radiation emerging from the illumination section.

Illuminators of this invention may have a fixed aperture that limits the transmission of radiation to a well-defined area such that the mix of wavelengths represents the sum of filter elements within that aperture. The amount of radiation at the peak transmission wavelength may diminish as additional filter elements of differing wavelengths are introduced into the radiation path. This design is simple and can use the maximum aperture area practical. In other embodiments, an aperture having variable area may be constructed that may increase in size if desired to allow additional radiation of differing wavelengths to be added to the original beam. Conversely, if it is desired to provide a narrower band pass, the aperture can be decreased in size to exclude undesired wavelengths from passing. This design can be used to keep the amount of radiation at peak transmission wavelengths approximately constant while adding radiation of differing wavelengths.

In other embodiments, selection of peak wavelength, bandwidth and/or intensity can be controlled by the use of a plurality of shutters positioned relative to a filter array. By opening certain shutters that are positioned corresponding to a desired peak wavelength, a beam of radiation can be captured that has that selected peak wavelength. In other embodiments, one can open up shutters corresponding to higher, lower, or both higher and lower wavelengths to permit the passage of radiation having a broader bandwidth. In yet other embodiments, one can open up a plurality of shutters corresponding to a peak wavelength to increase the intensity of radiation in an output beam. In still further embodiments, a plurality of peak wavelengths can be selected to provide multiple wavelength output beams. It can be readily appreciated that numerous variations of the above can be used to provide a large number of possible output beams.

The types of shutter mechanisms used are not crucial. In certain embodiments, one can use mechanical shutters that can be retracted to open up an aperture. In other embodiments, an array of mirrors can be used to reflect the beam of radiation toward a particular location. In still other embodiments, a shutter array can incorporate an electro-optical device, including by way of example only, liquid crystal devices (LCDs), Pockels cells, Kerr cells and other optical devices. In a shutter array, control over individual shutters can be accomplished using mechanical or electrical signals, and those can, in certain embodiments, be controlled by a computer program.

C Pulsed Illuminators

In addition to providing radiation having controlled wavelength and bandwidth characteristics, the radiation may be provided in a continuous or pulsed fashion. Pulsing radiation can either provide a frequency of radiation that can be absorbed by different targets differently to achieve a desired degree of stimulation, or alternatively as a means for controlling the total dose of radiation emitted by the device. To provide pulses of radiation, any suitable mechanism that can regulate the pulse width (duration), the frequency, or the pattern of radiation pulses can be used. For example, in several embodiments, radiation can be passed through a shutter or interrupter system to provide the aforementioned radiation as pulses at variable frequencies. In a circular interrupter, a disk of opaque material having holes, slits, slots, or areas of transparency can be rotated about an axis perpendicular to the plane of the disk. A portion of the rotating disk can be placed in a beam of radiation, and during the time that a hole or transparent area is in front of the beam, the beam can pass through the disk, thereby providing the desired radiation. When an opaque portion of the disk is in front of the beam, the radiation is blocked from passing through. Advantages of pulsed radiation include increased efficacy of electromagnetic radiation therapy. For example, the use of different frequencies of radiation pulses has been demonstrated to affect nerve cells differently from muscle cells. The selection of the wavelength and frequency of the radiation can be based upon methods developed for each application.

An interrupter or shutter mechanism may be placed in the radiation path of an illumination section to provide intermittent pulses. An interrupter can be desirable if it transmits all of the radiation in the open state. The number of apertures in the interrupter and the rotational speed of the interrupter can determine the pulse rate. Low pulse rates may also be obtained by oscillating the interrupter aperture across the radiation beam. The rate that the interrupter is moved may be varied over time to produce a profile of radiation intensity vs. time. A single interrupter may be placed such that two or more radiation sources pass through the interrupter. The placement of the radiation sources, the placement of the center of rotation of the interrupter, and the number of apertures affect the relative timing of the pulses for each radiation source. Certain of these embodiments can have four apertures and two radiation sources placed symmetrically around the center of rotation such that the initiation of each pulse is concurrent for both entrance ports. Electro-optical shutters, including by way of example only, LCDs, may be used in place of the interrupter wheel to achieve similar results and add independent initiation of pulses and/or pulse profiling.

It can be readily appreciated that an interrupter or an electro-optical mechanism can be designed to provide any desired pattern of pulses. For example, in one series of embodiments, a circular disk having transparent areas arranged in arcs around the disk can be used in situations in which it is desired to have a repeated pattern of pulses. It can be appreciated that the arc length of a transparent area and the rotation speed can determine the duration and frequency of pulses. However, by providing transparent areas of differing configurations, for example, one having a relatively long arc length, and another having a relatively shorter arc length, a pattern of long and short pulses can be provided. It can also be appreciated that providing transparent areas that are equidistantly arrayed about the disk can provide a pulse frequency that is substantially constant. However, by providing transparent areas of differing distances from one another, one can select the pattern of radiation pulses. By altering the speed of interrupter rotation, the pulse rate can be varied.

During treatment of physiological of pathophysiological conditions, the oscillating interrupter can provide variable pulse width, variable frequency, and can be used to vary the wavelength. The configuration of transparent areas in an interrupter and the rotational speed of the interrupter can be adjusted to provide a wide variety of waveforms (see below).

It can also be appreciated that a pulse can have an abrupt onset or a ramped onset. By providing transparent areas that have a clean, or "sharp" edge, the onset of a pulse can be abrupt. However, by providing a wedge-shaped slot, or alternatively, a gradient transition between opaque and transparent areas, the onset of the pulse can be varied.

Moreover, in these embodiments, one can appreciate that providing a slower rotation can provide a prolonged transition period between "off" and "on" parts of the duty cycle and can provide longer durations of a pulse. Although different pulse patterns are described for mechanical interrupters, it can be readily appreciated that electro-optical interrupters can be used that can provide a wide variety of pulse patterns.

In certain embodiments, a sensor may be added to monitor the beginning of radiation pulses and functionality of the illumination section. Many devices and methods are available to determine the start time of a pulse. For example, a fiberoptic pickoff may be mounted next to the waveguide entrance port. The output of this pickoff may be used to monitor the wavelength and intensity of the radiation passing through the illumination section when coupled to appropriate sensors. The output may be passed through a narrow-pass filter to initialize a reference position or confirm the positional repeatability of the system. Another example is a sensor to determine the location of the interrupter apertures relative to the entrance ports. Pulse rate can be adjusted by the interrupter motor controller circuitry based on output of an encoder integral with the interrupter motor. The accuracy of the radiation pulse rate can depend upon the control circuitry and may have different ranges of acceptable accuracy for different applications.

In one series of embodiments of devices include a radiation source, filters and an optical system to deliver the filtered radiation to a waveguide, such as a fiberoptic element. Multiple radiation sources can be combined in the fiberoptic cable system and delivered to one or more radiation delivery ports. The routing of fibers determines the proportion of each wavelength at each delivery port.

D Multiple Beam Illuminators

Devices of this invention can utilize two or more radiation sources that may be of the same or different types. Typical radiation sources include incandescent lamps, arc lamps, and strobe lamps for systems that are intended to provide selectable wavelengths. Narrow spectrum devices, such as lasers or LED's, may also be used when the bandwidth dispersion is desirably narrow. Gas discharge lamps can have several wavelengths that are emitted which may also be useful, such as combining UV radiation with visible and/or infrared radiation.

A radiation source optical system may be as simple as a mirrored reflector behind the radiation source which can focus the radiation beam onto the waveguide. Additional optics may be incorporated as desired for the particular illumination system. For example, a broad area source, such as a strobe, may use a collecting or collimating lens system between the source and the filter. The characteristics of the radiation source reflector may affect the operation of the system. For example, a reflector maybe used which allows a high proportion of the infrared (heat) emitted by the radiation source to be transmitted away from the filter and waveguide.

E Waveguide/Fiber-Optic Cable Assembly

In certain embodiments of this invention, a waveguide or fiberoptic cable assembly can consist of multiple entry ports and one or more exit ports. Routing of the fibers can determine the proportion of radiation from each entry port to each exit port. The material of the waveguides or optical fibers is selected to permit passage of the desired wavelengths. For example, glass fibers may be used for visible and infrared radiation (400–1000 nm) while other materials, such as quartz fibers may be selected for ultraviolet radiation (200–400 nm). Many configurations and materials, including liquids, are possible. In certain embodiments, there can be two entrance ports and two exit ports. The fibers can be routed to provide one-half of the radiation from each entrance port to be directed to each exit port. This arrangement can provide the user with two radiation sources with similar multi-wavelength output.

In other embodiments, alternate fiber routing configurations may be used to provide different ratios of input to output. For example, a third entrance port may have a radiation source that does not utilize a filter system. This illumination section may provide output from a simple lamp to provide general illumination or may provide a source of ultraviolet radiation (or infrared, or other wavelength) that can pass directly into the entrance port of the waveguide with little attenuation. In other embodiments, a laser can be used to provide a narrow bandpass light source.

The output beam of electromagnetic radiation can be provided in a number of different desired shapes and configurations. For example, for certain therapeutic uses, it can be desirable to provide beams having rectangular, triangular, polygonal, circular, oblong, annular, or other desired shape. By arranging waveguides in any of the above configurations, a desired beam can be provided. By providing flexible waveguides, the different beams can be separately directed at different desired locations.

F Uses of Illuminators

The industrial utilization of this device includes many fields in addition to health care and treatment of disorders. The ability to control dominant wavelength and bandwidth width is, by way of example only, can be used for: (a) discriminating subtle variations in color characteristics for machine vision; (b) grading of material characteristics automatically, such as fruit ripeness, or paint reflectance; (c) microscope illumination for biological and industrial applications, fluorescence microscope; (d) as a catalyst in radiation triggered chemical processes; (e) simulation of radiation source and filter combinations; (f) testing of optical assemblies; and (g) dispersion characteristics of materials, especially optical materials and fiberoptics, (h) phototherapy using drugs tha require specific waveforms for activation. Certain of these uses are described more fully in the U.S. Patent Application titled "Therapeutic Methods Using Electromagnetic Radiation" Constance Haber and Allan Gardiner, Inventors, Attorney Docket No: WMAG 1010 US1 SRM/DBB, filed concurrently and incorporated herein fully by reference.

G Analysis of Temporal Data and Therapeutic Responses

Analysis of spectral and timing data from illuminators of this invention can be performed using a computer and a software package, either designed specifically for the purpose, or using commercially available software. A data filter in a commercial application including joint time frequency analysis using Fast Fourier Transform "FFT" as well as other deconvolution methods can permit correlation of spectral and time related data (pulse or chop) and physiological effects of electromagnetic radiation. In certain embodiments, measurements involve monitoring a radiation signal using the interrupter or electro-optical shutter to expose a part of a subject's body to radiation of a known wavelength, wavelength variation, bandwidth, pulse width, intensity, and pulse frequency. Simultaneously or at intervals, one can monitor effects of such radiation using, for example, the surface electromyogram (sEMG or SEMG), electroencephalogram (EEG), evoked responses and the like. An analog input can be provided into the computer, and the phase and frequency domain of the signal relative to output of interrupter signal can be determined using, for example LabView™ software. This can be used to determine the signal strength and the transit time for the signal to travel to the sensor. In addition, a system from Neurometrix can be used. The system consists of an interrupter, which can be run at a frequency of about 1 Hertz (Hz) to about 1000 Hz. In alternative embodiments, the interrupter can operate at a frequency of between about 1 Hz and about 500 Hz, and in still other embodiments from about 5 Hz to about 100 Hz. Using pulsed illumination a system can detect the presence of signal and the phase differences between remote locations on the body. This can permit comparison of transmission capability through excitable tissues, such as nerves, muscles, and connective tissues, in conditions such as, for example, diabetic neuropathy and other nervous disorders, especially disorders of the spine. Normal physiological responses can be obtained by studying subjects without specific disorders, or by studying unaffected organ and tissues of normal subjects.

Additionally, by comparing the above-obtained normal results with those obtained from subjects having specific disorders of excitable tissues and organs, improved diagnosis of those conditions can be provided. Additionally, by monitoring a subject's responses to electromagnetic radiation therapy over time, such as heart rate variability, SEMG and other real-time measurements, improved evaluation of the progression and/or treatment of those disorders can be provided. Additional discussion of specific disorders of excitable tissues is provided in the U.S. Provisional Patent Application titled: Therapeutic Methods Using Electromagnetic Radiation, Constance Haber Stevenson, D. C., and Allan Gardiner, P. E., inventors, filed concurrently, incorporated herein fully by reference.

EXAMPLES

The following of examples are intended to be for illustration only. Other embodiments of this invention can include variations of the systems and devices described. All of these other variations and combinations are considered to be part of this invention.

Example 1

Optical Illuminator I

In one embodiment, a device is provided that has two lamps with focusing reflectors, two rotary filter arrays and one interrupter wheel with four apertures. Control circuitry receives signals from the operator that provides (a) the intended brightness of each lamp, (b) the intended wavelength peak for each illuminator, (c) the intended wavelength spread for each illuminator, and (d) the intended frequency of output pulses, wavelength variation. The signals are processed and the appropriate actions are initiated by servo controllers. The signals from the operator may be locally developed through electronic and mechanical input devices or from a remote source such as a computer. The lamps in this embodiment are standard lamps used for 8 mm movie projectors. Lamp reflectors concentrate the radiation into a spot suitable for fiberoptic illumination. The filter is a pattern on a glass substrate that transmits radiation of varying wavelength depending upon its angular and radial position relative to the radiation beam. The filter is produced using a photolithographic method that allows individual areas of a few square microns to be individually manufactured with specific filtering characteristics. Further descriptions are provided with reference to FIGS. 1–18.

FIG. 1 depicts an embodiment 100 of this invention as described immediately above. Computer interface 104, receives input signals from an operator and provides outputs to lamp brightness control 108, which controls the current or voltage 112 to lamps 114 and 116. The brightness control can be any of a number of different types, including but not limited to a transistor control or a transformer with a radiation dimmer. Any means of adjusting the brightness of the lamps under computer control or manual control can provide illuminator beams having differing brightness.

Computer interface 104 provides signals to wavelength driver 120 and bandwidth driver 130 drives the motors 124 and 128 which position filter arrays (not shown) in series with lamps 114 and 116 to provide output beams 132 and 136 having desired peak wavelengths and wavelength bandwidth characteristics. The controls of driver 120 can be stepper motors or servomotors, or alternatively servomotors with closed loop encoders. A desirable feature is the ability to position filter arrays using motors 124 and 128 reproducibly to the same location relative to the lamps 114 and 116 such that the wavelength of beams 132 and 136 can be controlled from the host program through the computer interface 104. The wavelength driver 120 electronics can be a simple system using transistors or some of the micro controller chips, which provide position information, acceleration and deceleration. Motion controls are available commercially from vendors in a variety of industries to position radiation controlling devices. In the case of circular filter, the motor may be a direct drive to position the angle of the filter. In the case of linear filters then the motors may be connected to some other devices such as a lead screw or a rack and pinion system. A second motor is used to position the filter to control the bandwidth.

Computer interface 104 provides a signal to interrupter speed and position control 140, which regulates the position of interrupter servomotor 144. Interrupter 152 is a simple plate with slots in it or other holes 204. Interrupter 152 can be a glass disk with an emulsion that is opaque over part of the area with another part being clear. A simple embodiment includes a disk with slots in it with one, two, four or however many slots are appropriate in order to get the total speed range necessary to get the pulse rate required for the output. The limiting speed of the motor 144 is controlled by the interrupter speed position feedback controller 148 or by its own electronics. Servomotor 144 has an encoder which provides information to the controller 140 of how fast the motor is turning and the current position of the aperture(s) relative to the illuminator beam. A reference mark is used to initialize the location of interrupter 152 attached to servomotor 144 and can provide information about the timing of the pulse of radiation emitted by lamps 114 and 116. In this case the home position or reference mark could be used to know where the radiation is being transmitted through the interrupter 152. A computer program can control the interrupter speed position control to move the interrupter until the reference mark is located. At that point the counters can be zeroed or that mark in some other way tracked such that the location of the disk now can be reliably returned to that open position. Alternatively, or if that speed of the interrupter is tracked alone and not position then each time is desired to control the interrupter to be either opened or closed, the reference mark would be relocated.

The interrupter speed position controller 140 can be as simple as a voltage placed out to the motor which would cause the motor to turn at a desired speed. The control of that speed may not be as accurate as desired and in that case, a tachometer (not shown) can be used, and a servo amplifier that controls velocity could be implemented. Alternatively, a microprocessor can control the speed and also track the position of the interrupter 152 such that it would always come to rest in either an opened or closed position as desired by the operator. Using such a system, it can be desirable to monitor the output of the illuminator(s) directly, and not operate solely by presetting desired values of the variables. The beam may be interrupted by an electro optical shutter or mirror.

Wavelength sensors 160 and 164 can be used to monitor the wavelength of radiation of either one or both illuminators. For each lamp/filter assembly, one sensor is shown, although two or more sensors maybe used if desired. Each sensor 160 and 164 is associated with a narrow bandwidth filter, having bandwidths in the range of a few nanometers. Computer software 156 in the hardware would be used to find a peak value of wavelength. For instance, if the wavelength drivers 120 position filter 124 and 128 to a desired wavelength and the interrupter 152 is positioned so that the radiation is being transmitted, then the wavelength sensor 160 can determine whether the desired wavelength is detected. If the observed wavelength is not as desired, then the computer interface 104 can provide signals to driver controller 120 to adjust the position of filters 124 and 128 to produce the desired wavelength of output beams 132 and 136. Combinations of peak bandpass and bandwidth settings may be used to calibrate the system.

The system described can allow for ongoing calibration and confirmation that the wavelength, wavelength bandwidth and other variables remain as desired. Combinations of peak bandpass and bandwidth settings may be used to calibrate the system. In alternative embodiments, one can provide multiple sensors sensitive to different portions of the filter array. That way the system could drive the filter to wavelength number one, find the peak, find the calibrated location that matches wavelength number one, and then repeat the process for wavelength number two. All of the intervening wavelengths could be determined by calculation relative to those two calibration points.

The first time that the system is used, it can be calibrated using another device to interpolate the positions in between two calibration points. And then later, the relative positions of wavelengths can be used to confirm that the computer now has confirmed control over wavelength. Additionally, the speed of the interrupter could be measured by moving the filter to one of the wavelengths and using the feedback to the computer to determine that the frequency of the interrupter indeed matches the expected frequency being programmed by the computer interface. In the machine design it can be desirable to allow the machine to self-test upon start up or at any time there is some question about the accuracy of the system. By providing feedback, the system can do this self-calibration. A sensor which is sensitive to a wide range of wavelengths may be used during operations to detect the presence of radiation for timing purposes.

Figure 2A:
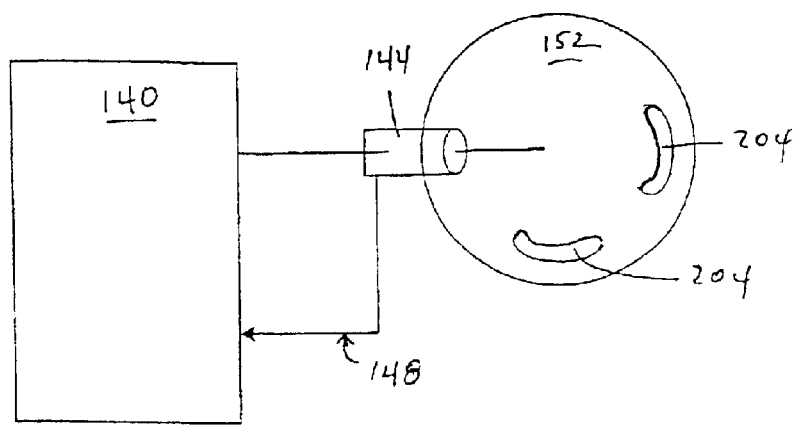
FIGS. 2a–2b depict a schematic drawing two views of a portion of an illuminator of this invention.

FIG. 2*a* depicts a schematic diagram of the interrupter speed/position controller 140 as depicted in FIG. 1. Interrupter speed position control 140 is attached to the servomotor 144. Encoder feedback 148 can provide the system with more speed range and stability of speed. The interrupter disk 152 has two slots 204 shown.

Figure 2B:
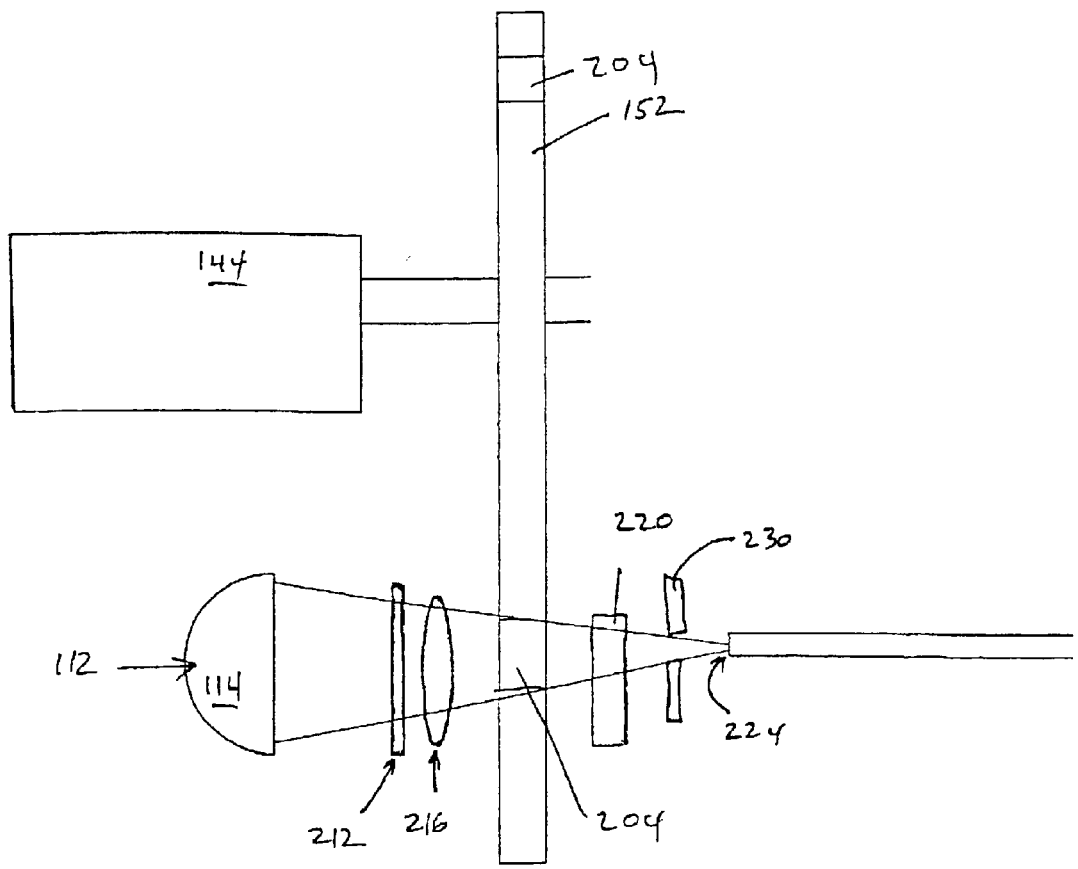

FIG. 2*b* depicts a side view of the interrupter 152 as shown in FIG. 2*a*. Interrupter 152 is depicted on a shaft of servomotor 144. The disk of interrupter 152 is shown in the path of electromagnetic radiation produced by lamp 114. Output of lamp 114 is controlled by the output of power controller 112, and is focused by lens 216 and heat-absorbing filter 212, which maintains the output beam receiver 224 at a desired temperature. The beam passes through slots 204 of interrupter disk 152 and the output passes to filter 220. The output beam then passes through the aperture 230 to waveguide 224 for transmission remotely to the desired site of illumination. Relative placement of the heat absorbing filter 212 and the lens 216 can depend on the configuration of lamp 208 and waveguide 224. In certain embodiments, lens 216 and heat filter 212 may not be required at all. The elements can be placed in other relationships, depending on the desired configuration. For example, in certain embodiments, the beam may pass through a filter and then the interrupter. In other embodiments, more than one waveguide may be used, in which radiation gathered after passing through an interrupter can be transmitted remotely to a filter, and then pass through a filter. If desired, another waveguide can then gather the filtered radiation for transmission to a remote site for illumination.

Example 2

Rectangular Filter Array

Figure 3D:
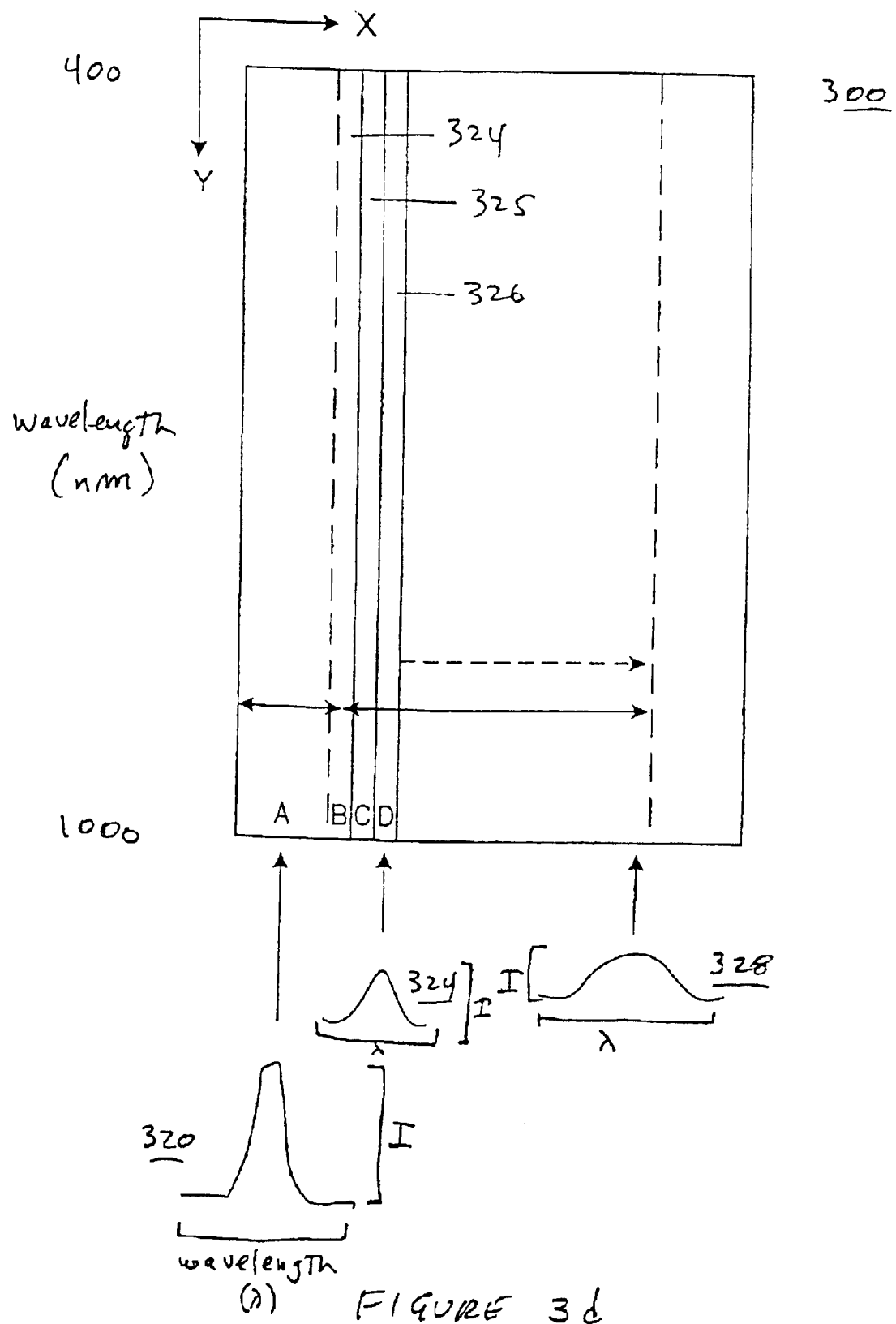

FIGS. 3a–3h depict the relationships between lamps, filters and waveguides of embodiments of this invention having rectangular filter arrays. FIG. 3a depicts a side view of an embodiment of this invention with no restricting aperture, including lamp 208, filter array 220 and waveguide 224. FIG. 3b depicts an embodiment 300 of a parallel filter array of this invention having two axes. The vertical dimension of filter array 300 comprises filter elements arrayed according to peak wavelength, from 400 nm on the top to 1000 nm on the bottom of filter 300. The left side of filter 300 has areas of narrow bandwidth, in which the individual filter elements have narrow bandwidth characteristics. Toward the right side of filter 300, the bandwidth of the filter is increased, so that radiation passing through those areas has a wider bandwidth characteristic.

Thus, to provide radiation having a desired peak wavelength and a narrow bandwidth range, a source beam 224 is aligned with a portion of the filter 300 on the left side, where the bandwidth is narrow. Then, by moving the source beam 224 vertically, one can select the peak wavelength desired. FIG. 3c depicts schematically a portion 304 of a filter of this invention having narrow bandwidth range. By moving the filter relative to the source beam 224 vertically in this diagram, the wavelength can be selected. One can readily appreciate that the bandwidth characteristics of this type of embodiment can be selected by providing source beam 224 having dimensions that are greater than the size of an individual filter element. Thus, in embodiments in which source beam 224 passes through several filter elements, each having a different peak wavelength, then the output beam can have a series of wavelengths corresponding to those wavelengths of the filter elements so provided.

FIG. 3d depicts in more detail, an embodiment 300 of this invention having a rectangular parallel array of filter elements. As depicted in FIG. 3b, rectangular filter 300 has a vertical axis having individual filter elements arranged in order of increasing peak wavelength, from top to bottom, from 400 nm to 1000 nm. The horizontal axis has a left portion A in which the wavelength bandwidth is constant at any particular vertical position in the filter. A relatively narrow bandwidth 320 of portion A is depicted below portion A. To the right of portion A, portion B is provided that has a broader bandwidth than that of portion A. An intermediate bandwidth 324 of portion B is depicted below portion B. Similarly, portions C and D are provided that have progressively greater bandwidths, such as depicted by spectrum 328. Thus, by moving the different portions of filter 300 across a source beam horizontally, different bandpass characteristics can be provided.

Figure 3E:
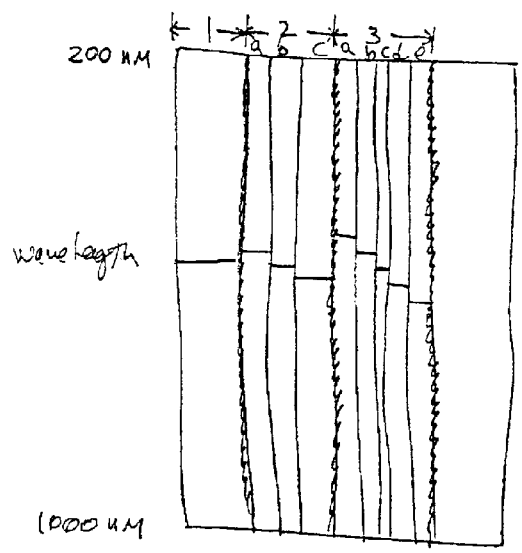

FIG. 3e schematically depicts an embodiment of this invention illustrating rectangular filters which can provide selectable wavelength bandwidth characteristics for a beam of electromagnetic radiation. In this embodiment, the wavelength bandwidth is selected by positioning a source beam relative to one of a series of different tracks, here labeled 1, 2 and 3, each of which comprises vertical filter arrays comprising elements having narrow bandwidth characteristics. In a first area 1, for any vertical position, the peak wavelength is uniform across the horizontal direction, and is represented by a horizontal line. An adjacent vertical filter array 2 is comprised of 3 identical filter arrays 2a, 2b and 2c. Each of the individual filter arrays are as depicted for area 1 except that the peak wavelength in area 2a is off set or displaced to shorter wavelengths by a fixed amount, by way of example, only, 10 nanometers in wavelength, and area 2c is offset by a similar amount but to the longer wavelengths. Area 2b is identically arranged as area 1. Area 3 is otherwise identical to areas 1 and 2, but comprises 5 discrete vertical filter arrays, 3a, 3b, 3c, 3d, and 3e, with arrays 3a, 3b, 3d, and 3e offset with respect to area 3c.

Figure 3F:
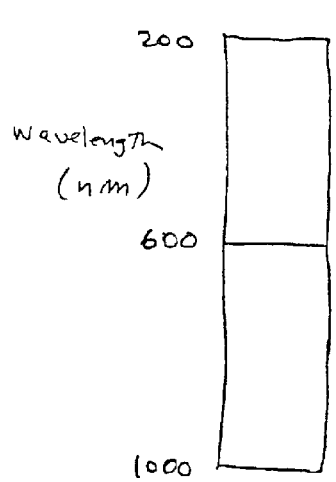
Figure 3G:
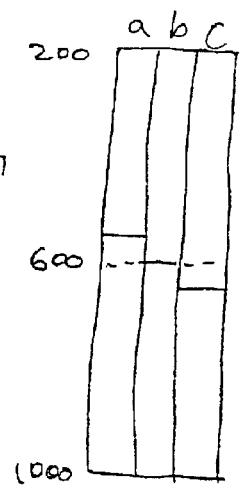
Figure 3H:
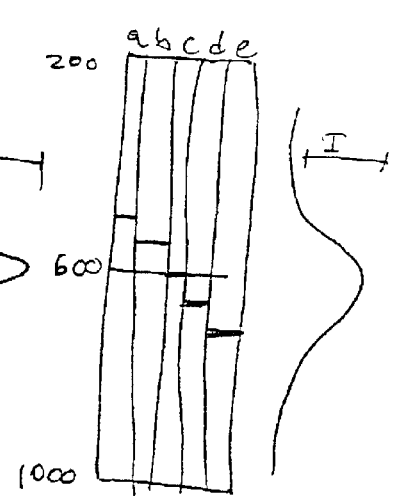

For example, as illustrated in FIGS. 3f, 3g and 3h, the peak wavelength is shown as 600 nanometers for three different bandwidths. In FIG. 3f, a single vertical array is present having a narrow bandwidth, and producing a relatively sharp peak in intensity of radiation (I) at 600 nm. In FIG. 3g, three vertical arrays of filters are represented as 3ga, 3gb and 3gc. Vertical array 3gb is in the same position as the array shown in FIG. 3f, whereas array 3ga is offset to smaller wavelengths, and 3gc is offset to longer wavelengths. Thus, radiation passing through area 3ga has a peak wavelength of 590 nanometers and that passing through area 3gc has a peak wavelength of 610 nm. If an aperture for a source beam is sufficiently large to encompass areas 3ga, 3gb, and 3gc, then the radiation passing through the filter will comprise one portion derived from area 3ga, one portion from area 3gb, and one portion from area 3gc, and therefore having a broader bandwidth than that obtained for FIG. 3f.

FIG. 3h depicts a series of areas 3ha–3he of vertical filter arrays of this invention. As with FIG. 3g, radiation passing through all 5 areas with have a peak wavelength of 600 nm, but with a bandwidth greater than that of FIG. 3g.

Figure 3I:
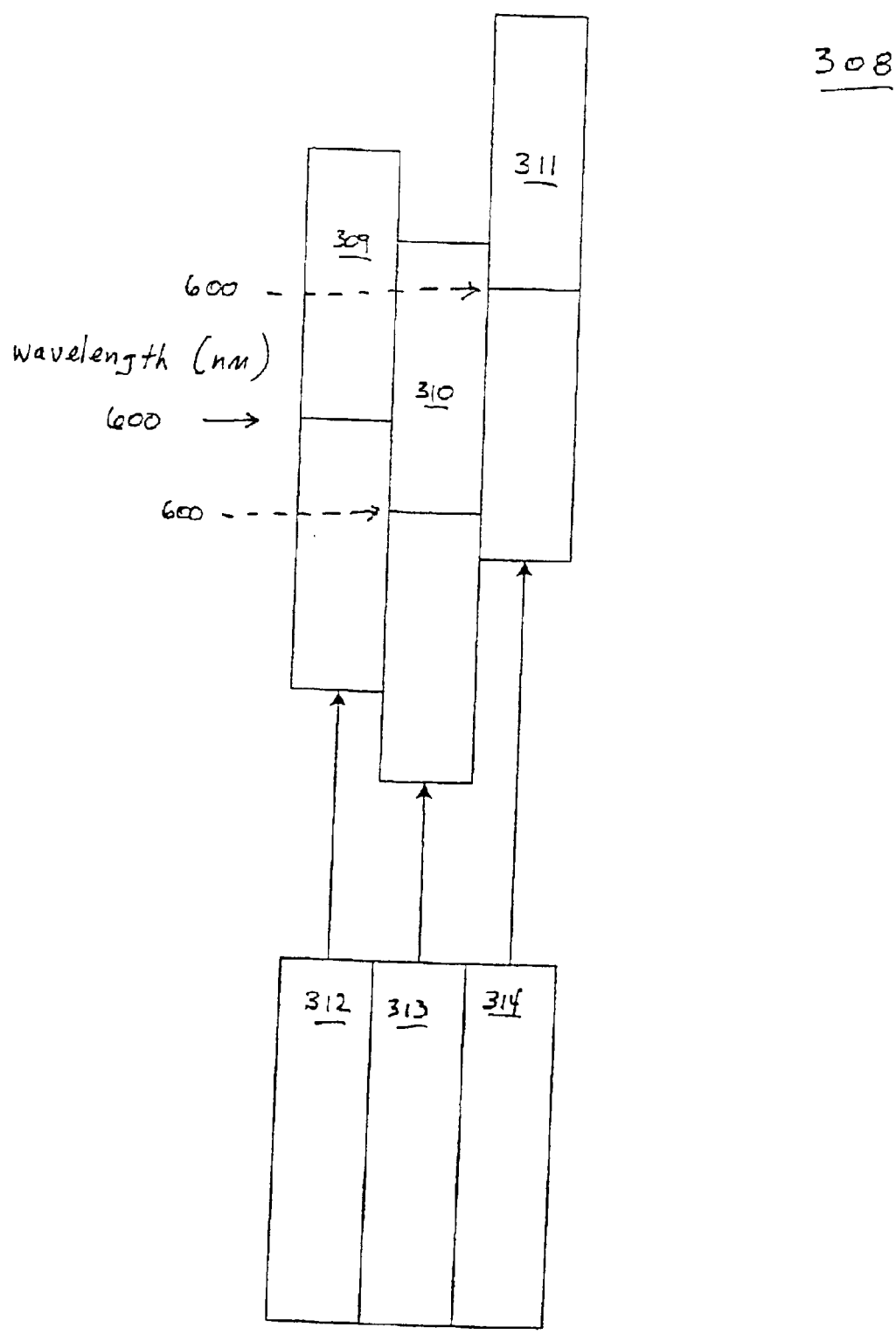

FIG. 3i illustrates an embodiment 308 of a variable bandwidth mechanism of this invention. Three filter arrays 309, 310 and 311 each have a peak wavelength of 600 nm. Filter arrays 309, 310 and 311 are depicted being moveable relative to each other by motors 312, 313 and 314. In FIG. 3i, filter array 309 is depicted having a peak wavelength of 600 nm in a relatively central position relative to arrays 310 and 311. In contrast, array 310 is offset by motor 313 below array 309, and array 311 is offset above element 310 and 309.

It can be appreciated that other configurations are possible and can comprise multiple different areas. It can also be appreciated that the offset of individual areas not need be the same, so that in certain desired wavelength regions, the bandwidth can be larger or smaller than the bandwidth in other wavelength regions. It can also be appreciated that by adjusting the aperture size, more or fewer regions of each area can be placed in the path of the source beam and can produce radiation having different wavelength compositions.

As the filter is moved in front of the aperture or waveguide bundle, the amount of radiation for each wave length could be controlled by moving the filter in the vertical direction to control the central or peak wavelength and in the horizontal direction to control the bandwidth spread. By designing the widths of the vertical filter arrays and their offsets, the ability to control the wavelength spread can be programmed into the controller so that the host program can send controls to position different filter areas, apertures or sources of the beam to provide a high degree of control over the composition of the radiation emitted by the illuminator.

It can also be appreciated that an aperture or waveguide bundle can be asymmetrical, having, for example a rectangular cross-section. Thus, if the same bundle were rotated 90 degrees, for example, then the wavelength spread could be varied.

By way of illustration for a linear filter, if the distance between the area having a peak wavelength of 400 nanometers to that having 1000 nm were six inches long, there would be 100 nanometers per inch. If the diameter of the source beam were a quarter of an inch (0.25"), source beam would have approximately 25 nanometers spread in the wavelengths. For a rectangular source beam, the intensities of the wavelengths within the spread of 25 nanometers would be different from the intensities with a circular aperture. However, for a curved (e.g., circular or ovoid) source beam, the distribution of wavelengths would be different. The distribution of a circular beam source would be much more centrally weighted than for a rectangular source beam. It can be appreciated that if the admitting aperture or waveguide were a narrow rectangle across the filter area, then the wavelength spread would be much narrower.

Example 3

Circular Filter Arrays

Figure 4A:
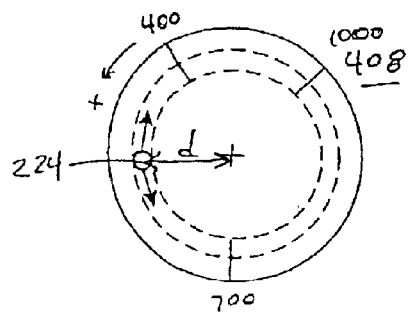
FIGS. 4a–4c depict embodiments of this invention having circular filter arrays.
Figure 4B:
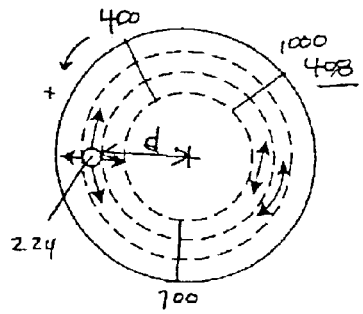
Figure 4C:
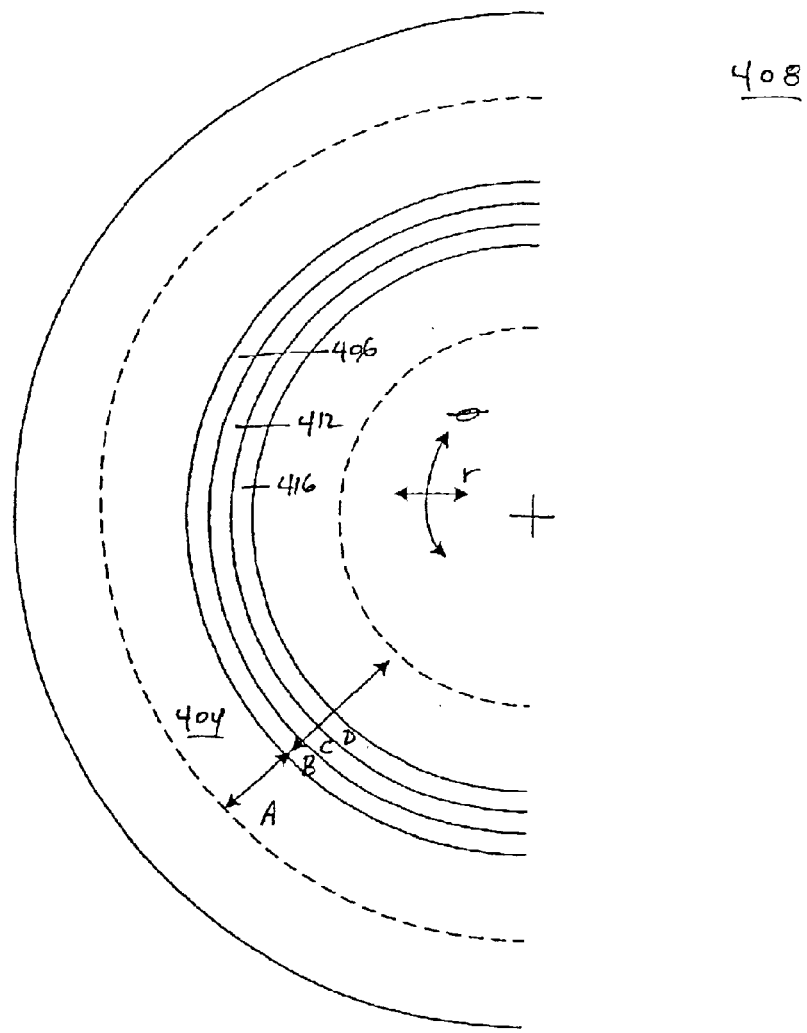

FIGS. 4a–4c depict an alternative embodiment of this invention 408 comprising a circular filter array. In FIG. 4a, individual filter elements are arrayed circumferentially about the central axis of the filter 408. At a given distance d from the central axis, an array of individual filter elements is provided in a fashion similar to those shown in FIGS. 3b and 3c, but rather than being linear, they are circular. Thus, by providing source beam 224 at distance d from the central axis, a particular series of filter elements can be exposed to the beam. By rotating the filter 408 about its axis, the wavelength of the radiation can be adjusted, in this case, between 400 nm and 1000 nm.

FIG. 4b depicts an embodiment of this invention in which different regions of filter 408 have different bandwidth characteristics. In this embodiment, an area more central to the axis d1 has relatively larger bandwidth characteristics than a more peripheral area d2. Thus, if a relatively narrow bandwidth is desired, source 224 can be positioned more peripherally on filter 408, and if a relatively narrower bandwidth is desired, source 224 can be positioned more centrally on filter 408.

FIG. 4c depicts additional details of a circular embodiment 408 of a filter of this invention, as shown in FIGS. 4a and 4b above. As with FIG. 3e above, there are areas of filter 408 defined by a distance from the axis r. In area 404, the bandwidth is relatively narrow and is constant with r. However, in areas 406, 412 and 416, respectively, the bandwidth increases progressively as distance r decreases, in a fashion similar to that of FIGS. 3e–3h.

The selection of wavelengths for a given position or angle in a rotary filter may also be selected to be a very different wavelength characteristics if the combined output of the optical system requires wavelengths that are of significant differences in the spread. Tracks A, B, C and D can be varied in other ways also. For instance, by way of illustration only, track A could have a peak wavelength of 700 nanometers, track B could be set to have a peak at 500 nanometers. The combined beam can have a combined wavelength spread that is much larger than simply a single wavelength with its usual distribution. The multiple wavelengths achieved in this way can provide colors which are not available as pure colors when perceived by the human eye. The same effect of multiple colors can also be achieved by having an illumination source set at one wavelength and another set to a different wavelength so that the combined output of the two and now go and mimic any color. Embodiments incorporating this strategy can be expanded to include 3 colors providing red, green and blue, or even more different wavelengths.

One advantage of circular embodiments is that controlling the position can be simpler than controlling a two-dimensional array as for the embodiments depicted in FIG. 3. In circular embodiments, the angular position can be controlled by direct drive on a motor, and then angular position can control the peak wavelength. The wavelength spread can be controlled by moving the center of rotation of the disk relative to the radiation path in the radial direction. In the case of the rotary filter the tracks are again designed such that the relative placement of the optical path can select either a narrow spread or a wider wavelength spread. Circular embodiments can have an added feature of a longer filter path, depending on the circumference of the disk rather as simply a linear device. Other advantages of circular embodiments include the possibility that the size of the total assembly can be smaller than rectangular arrays because the filter can be positioned angularly and translated in one axis only. The position of the source beam can be changed by a simple mechanism controlled by a stepping motor or servo-motor to move the beam radially with respect to the center of the disk. These motors can be controlled by the computer interface as depicted in FIG. 1.

There are a variety of manufacturing techniques which can produce filters suitable for the illuminators of this invention where there are tracks or areas which have different wavelength characteristics. In embodiments having fixed filter elements, individual elements can be deposited on plastic, glass, quartz or other substrate in areas which can be addressed as X, Y coordinates for rectangular arrays as in FIG. 3, or as angle θ and radius r from an axis of rotation for circular arrays as depicted in FIG. 4c. In certain embodiments, the output radiation can have a graduation of wavelength and wavelength spread. In other embodiments, changes in wavelength can be more rapid, or even in a step-wise or saltatory fashion. In certain embodiments, the filter can move while the waveguide and lamp assembly are stationary, and in alternative embodiments, the source beam can move and the filter array can remain stationary. Additionally, if desired, a rectangular aperture or other non-circular aperture can be used along with a mechanism which can rotate the aperture relative to the vertical filter arrays, and in that way even a wider variety of wavelength spreads could be available from the system. Moreover, because the embodiments described herein can be controlled by external signals, each configuration can be programmable and the composition of the radiation emitted by the illuminators can be repeatable.

In other embodiments, an array of liquid crystal shutters can be positioned over a filter array. By selectively opening one or more shutters, radiation can be selected. Embodiments of this type can be especially useful in situations in which it is desirable to have devices with a minimum number of moving parts, or in situations in which rapid electrical control over emitted wavelengths is desired.

Example 4

Waveguides and Output Beams

Figure 5A:
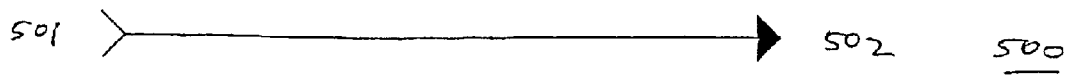
FIGS. 5a–5e depict embodiments of this invention having different mixtures of output from illuminators.
Figure 5B:
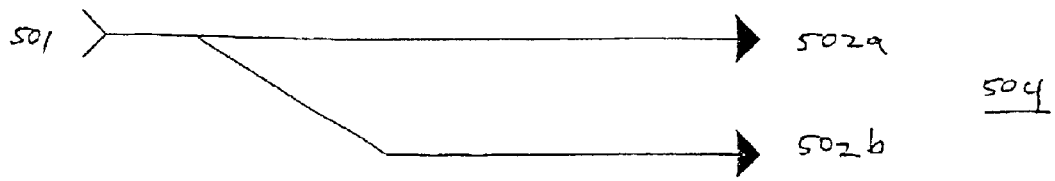
Figure 5C:
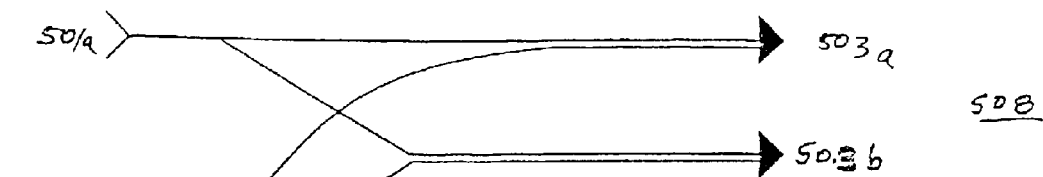

Once an output beam is created having certain wavelength, wavelength bandwidth, pulse duration and pulse pattern, the output can be directed to a desired location using waveguides. For example, waveguides can be in the form of a fiber optic cable as depicted in FIGS. 5a–5e. FIG. 5a depicts a simple, single waveguide 500 having an input end 501 and an output end 502. FIG. 5b depicts an alternative embodiment of this invention 504 in which a single input beam 501 is split into two output beams 502a and 502b. FIG. 5c depicts an embodiment of this invention 508 having a dual mixer cable where some portion of each input beam 501a and 501b goes to each of the two end effectors 503a and 503b. The ratio for the output maybe any desired value, for example, from about 1%: about 99% to about 50%: about 50%, or alternatively about 99%: about 1%. There is no limitation in proportion as long is there is some portion of each lamp source being mixed in the alternate output.

Figure 5D:
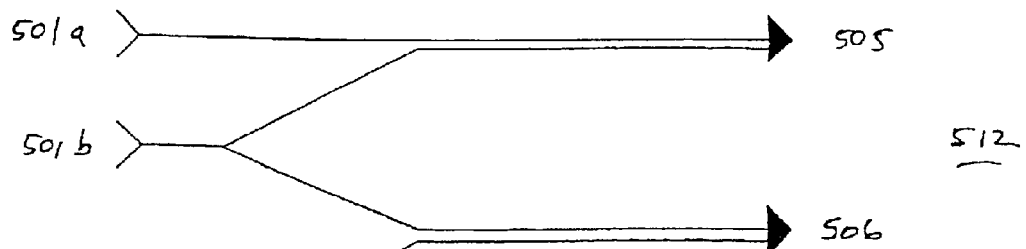
Figure 5E:
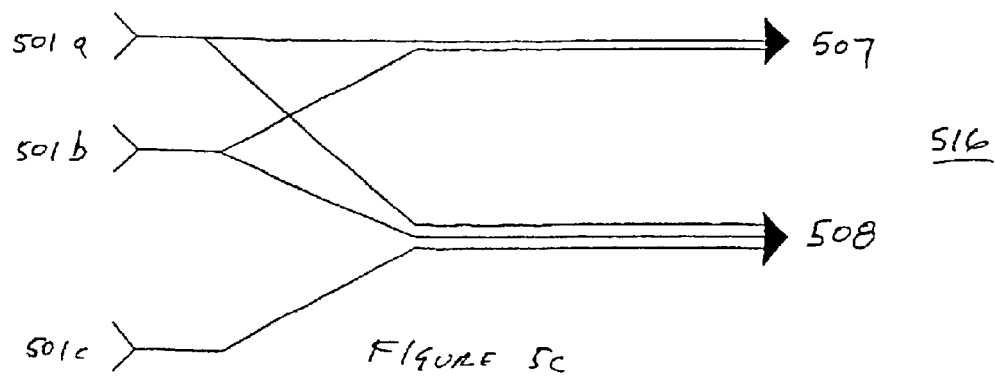

FIG. 5d depicts an embodiment 512 in which three inputs 501a, 501b, and 501c are mixed to provide two outputs 505 and 506. As with FIG. 5b above, the ratio of the components of the output beam mixture can vary from about 1%: about 99% to about 99%: about 1%. FIG. 5e depicts another embodiment of this invention 516 where three inputs 501a, 501b, and 501c are directed to one or more of the outputs 517 and/or 518. In this embodiment, inputs 501a and 501b are directed to outputs 507 and 508, whereas input 501c is directed only toward output 508. This type of configuration permits additional wavelengths to be mixed (a "mixer").

In certain embodiments, fiber optic cables can be desirable because fibers from one illuminator port may be directed to the other fiber optic cable. For applications that do not require fiber optic cables, the beam from the source and filter can be transmitted via an optical path which could include mirrors and beam splitters to combine radiation from multiple lamps. In other embodiments, fiber bundles having mixed fiber types can be used to transmit radiation having differing wavelengths. For example, to transmit both visible radiation and ultraviolet radiation, one can use plastic or glass fibers to transmit the visible wavelengths, and can use quartz to transmit the ultraviolet wavelengths.

Example 5

Configurations of Output Beams

Once an output beam has been produced, the beam can be delivered to a site using any of a number of different end effectors. FIGS. 6a–6g depicts a variety of end effectors 600. Common types of end effectors are available from fiber optic light source manufacturers. FIGS. 6a1–6a3 depict embodiment 604 having a source 601 and a "dental end" with a 45-degree bend (FIGS. 6a1 and 6a2), or alternatively a 90-degree bend (FIG. 6a3), or a bend at any desired angle. These can be simple light pipes made with fiber optics, which can be relatively resilient and can direct the radiation at a convenient angle. These can be made to be replaceable and/or reusable after sterilization, such as in an autoclave. Dental ends can be obtained from one or more commercial sources.

FIGS. 6b1 and 6b2 depict an embodiment 608 of this invention comprising an input beam 601 and an annular or ring light 602. Such "ring lights" can be commercially available and can distribute a bundle of receiving fibers by means of a mechanical housing or assembly to output light from an annulus "ring" of fibers.

FIGS. 6c1 and 6c2 depict an alternative embodiment 612 of this invention comprising an input beam 601 and a series of fibers distributed to form a "line" 603, or to form a rectangle or other shape that is desired.

FIG. 6d depicts an embodiment of this invention 616 that comprises an input beam 601 an output beam 605 and a lens 606 to focus the output beam. In an alternative embodiment shown in FIG. 6e, lens 606 can be used to collimate the beam.

FIG. 6f depicts 4 different shapes of output beams. A square configuration is depicted by effector end 630, a horizontally aligned rectangular end 634, a vertically aligned rectangular end 638, anc circular end 642 are shown. However, it can be appreciated that numerous other shapes of effector ends can be used advantageously.

FIG. 6g depicts an embodiment 624 of this invention that uses two separate input beams 601a and 601b, and two lenses 605a and 605b to focus two output beams 607a and 607b on a target. It can be readily appreciated that more than two end effectors may be used. Input beams 601a and 601b can have the same wavelength characteristics or can have different characteristics. By providing different wavelength inputs, a gradient of wavelength intensities can be generated where the two (or more) output beams interact. When this device is placed near an object to be illuminated, such a human finger during therapeutic applications, a gradient of wavelength interaction throughout a zone within the tissue is illuminated. One purpose of this gradient is to allow a continuum of interaction based on relative strength of two or more different wavelengths. A wavelength gradient can be desirable for treating conditions where different wavelengths cause different biological interactions. The ability to combine the two wavelengths in a graded fashion can permit the illuminated tissues to experience combinations of stimuli. This can be especially useful when the precise ratio is not known for maximum therapeutic affect. Alternative constructions of the applicator can use either line effectors, ring effectors, rectangular effectors or effectors having any other desired configuration. Any of the applicators can be moved relative to one another and across tissue to increase the area of tissue illuminated.

In certain applications, an effector configuration can use two line outputs arranged relative to each other such that the lines are parallel with overlapping regions of radiation. An intensity/wavelength gradient can be developed between the lines along a parallel zone beyond the effectors to increase the volume of the tissue exposed to the radiation. The spacing and angle of the effectors can determine the gradient zone.

In applications in which an effector configuration uses two concentric rings, each with a separate source, an intensity/wavelength gradient can be developed between the rings beyond the effectors. The spacing of the rings can determine the gradient zone.

Any of the applicators may be supplied by dual or mixing type fiberoptic cable assemblies which can have additional characteristics such as delivering the same wavelengths or combination of wavelengths to both effectors. This application may be used to provide more energy at the selected wavelengths determined by the fiber optic cable configuration.

Variations on these applicators may concurrently deliver energy by means of dental effectors, for instance, to the inside and the outside of the mouth. A mechanical housing can align the sources so that they remain in alignment while the applicator is moved. This method can provide the maximum amount of illumination to the full thickness of the side of the mouth. Use of single cables can permit uses in which one wavelength is directed inside the mouth and a different wavelength is directed outside the mouth, if desired. Use of a mixing cable can provide the same or similar wavelengths on both sides of the affected tissue. This same general scheme can be extended to have more than two radiation inputs if multiple wavelengths are desired.

Example

Vascular Imaging

Figure 7:
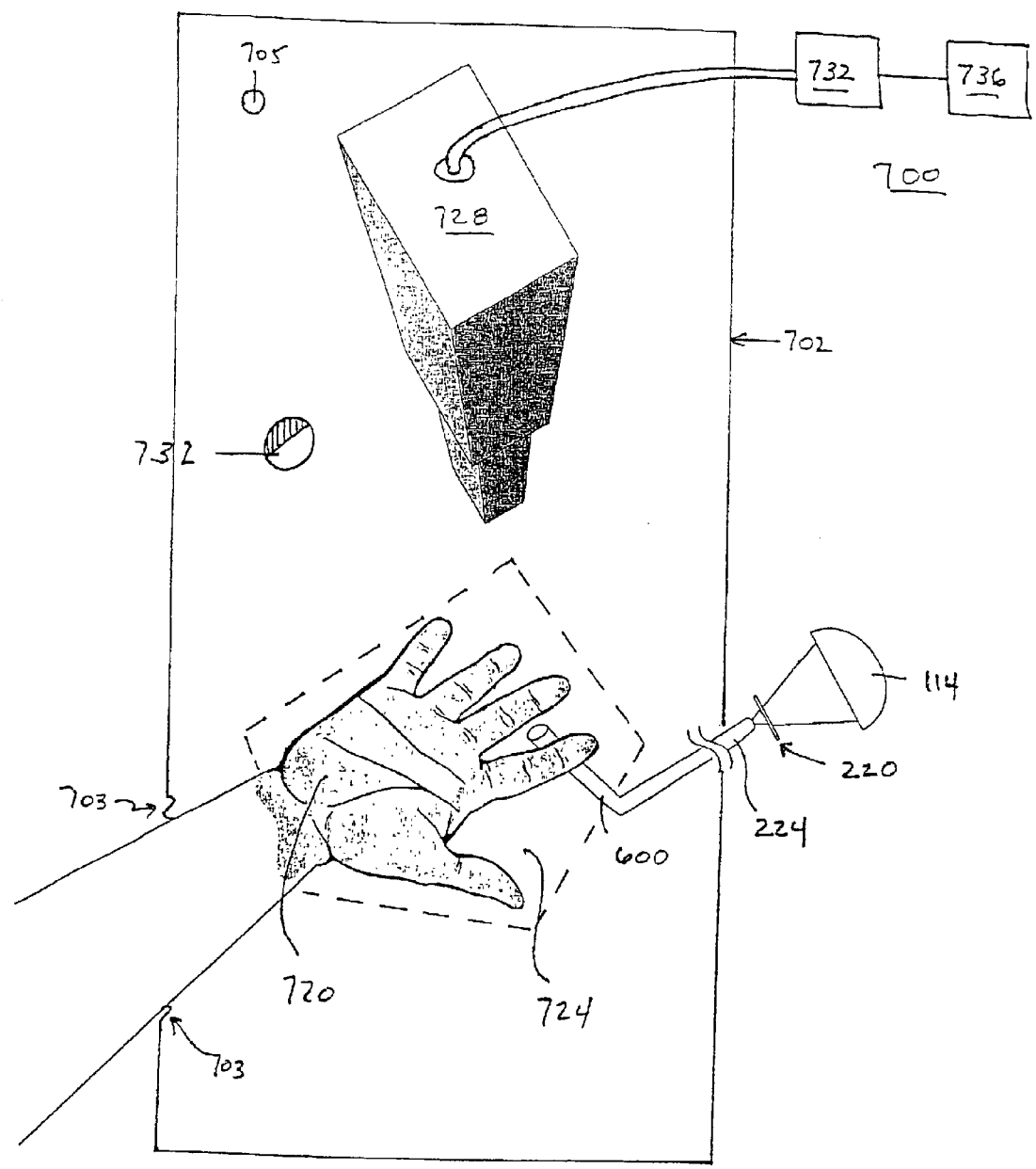
FIG. 7 depicts the use of an illuminator of this invention to monitor vascular function in a subject's hand.

Devices and systems of this invention can be used for vascular imaging. In certain embodiments of this invention a body part can be transilluminated. FIG. 7 depicts an embodiment 700 of this invention used for this purpose. The system comprises a lamp 114, a filter 220, a waveguide 224 an end effector 600 as described above. A body part, for example, hand 720 is placed on support 724 and radiation passing through hand 720 is detected using camera 728. The end effector 600 hand 720, calibration source 732 and camera 728 are depicted housed in a radiation-tight box 702, with a radiation-tight curtain 703. In operation, the hand is place on a support 724, and there can be additional registration pins or bumpers (not shown) which can allow the hand to be placed initially without the person being required to be very precise. The inside of the cabinet can be illuminated by an additional lamp 705 to provide visual feedback while positioning the hand. The actual field of view of the camera determines the size of the image relative to the total field. The camera signal is processed by a signal processor 732 which can control brightness and contrast, or any other variable of the video signal desired in order to produce the best image possible.

The output of the signal processor goes to display 736, a recorder (not shown), or other desired instrumentation. In use, this system can provide scanning through wavelengths typically in the 600 to 650-nanometer wavelength range to find the wavelengths that are most strongly absorbed by the particular person's vascular system. The wavelength can be changed while observing the output of the camera, either before or after signal processing, in order to find the particular wavelengths which provides the best contrast and visibility of the vasculature within the hand. The location observed on a particular finger or web of the hand can be selected for vasculature observation. More than one illumination source may be desirably provided so that more radiation is available for illumination through the body part.

The camera gain and offset can be controlled and standardized using a calibration target 732 which can permit the system to be returned to the same settings after treatment. By providing reproducible initial conditions of observation, the hand can be placed into the machine again and secondary pictures may be taken. The change in observed blood flow can be used to monitor treatments which increase or decrease blood perfusion. For instance, if the feet are placed in cold water or ice water, the blood flow to the hands may diminish over a period of time. Such diminishing flow can be observed through the video system.

In preliminary experiments, tests have been performed using a wavelength of 625 nanometers. Initial results indicate that there are substantial variations in absorption between individual people. This same apparatus can be configured to accept a foot in which case people with circulation problems of the feet such as people with diabetic neuropathy can be observed for changes in blood flow during and/or after treatment. For the feet, certain blood vessels are located on the bottom of the toes and the apparatus of this invention can be configured such that the camera is on the bottom of the foot and the illumination comes down from the top. The configuration of the illuminator and the camera can permit transmission of radiation through the tissue for observation by the camera. Experiments have shown that radiation around 600 to 650 nanometers appears to be strongly absorbed by blood vessels which provide imaging capability. Radiation of shorter wavelengths tends to be absorbed more uniformly and thus the contrast measured using shorter wavelengths can be diminished. Wavelengths longer than optimum are absorbed less and again contrast can be diminished. The optimum wavelength is dependent upon the absorption characteristics of the particular person. Oxygenation of the blood also affects the wavelengths absorbed. There may be several wavelengths of interest and this apparatus can provide measurements using more than one wavelength. In certain embodiments, the apparatus of this invention can be used to is observe blood vessels at different depths below the skin.

A black and white camera with broad low radiation level spectral sensitivity can be used to allow varying the wavelength over a wide range ("sweeping") to determine the desired wavelengths that are best transmitted through bulk tissue and also those that can be absorbed by the vascular system. Some cameras possess infrared sensitivity to wavelengths longer than 700 nanometers and/or have the capability of having a filter removed from the optical system which allows the detector, such as a CCD array, to receive the infrared radiation. In this case it can be desirable to use the infrared portion of the radiation spectrum rather than the visible portion because different features within the finger, hand or toe can be studied using different wavelengths. The ability to select a wavelength and have sufficiently intense radiation pass through substantial thicknesses of the body can permit observations that cannot made with normal full spectrum radiation.

The repeatability of this system can be improved by including means of self-calibrating the system and adjusting for brightness. These elements are not shown in FIG. 8. One such element can include an integrating sphere with a standardized sensor in it. An integrating sphere can be moved into a location to receive radiation from the end effector or optical train built into the cabinet. The power or intensity of radiation could then be adjusted and standardized for each wavelength by removing the hand or other body part from the radiation path and doing a calibration based on the particular wavelength. Standardized laboratory techniques can be used to carry out this calibration. Similarly, calibrations of the video camera can be accomplished using targets of known illumination. In certain embodiments, targets can have areas which are either clear or opaque, or may have steps of opacity which may be moved in front of the camera to measure the apparent brightness of the radiation source. The placement of these accessories and the precision of their motion can be designed to allow repeatability and accurate calibration of measurements with the device.

Larger body parts, such as the thicker parts of the hand or even the thinner portions of the leg may be imaged using a very intense radiation source and a very sensitive camera. Thus, measuring and/or imaging is not restricted solely to thin body tissues such as fingers or toes. Finer detail is generally seen with the thinner body parts because the vasculature that is being imaged is close to the surface. The optical density of the tissue and its ability to transmit or conduct radiation at varying wavelengths is dependent on the individual. Individuals with very fine vasculature throughout the hand, for instance, can appear very opaque compared to people who have large veins and tissue which readily conducts certain wavelengths of radiation, such as 625 nanometers. One can also use embodiments of this invention to transilluminate a body part at one wavelength and then observe that body part at a different wavelength. Using the systems and measurement methods of this invention can permit detecting certain responses of the vascular system to therapeutic intervention.

Example 7

Integrated System for Controlling Illuminator Function

Figure 8:
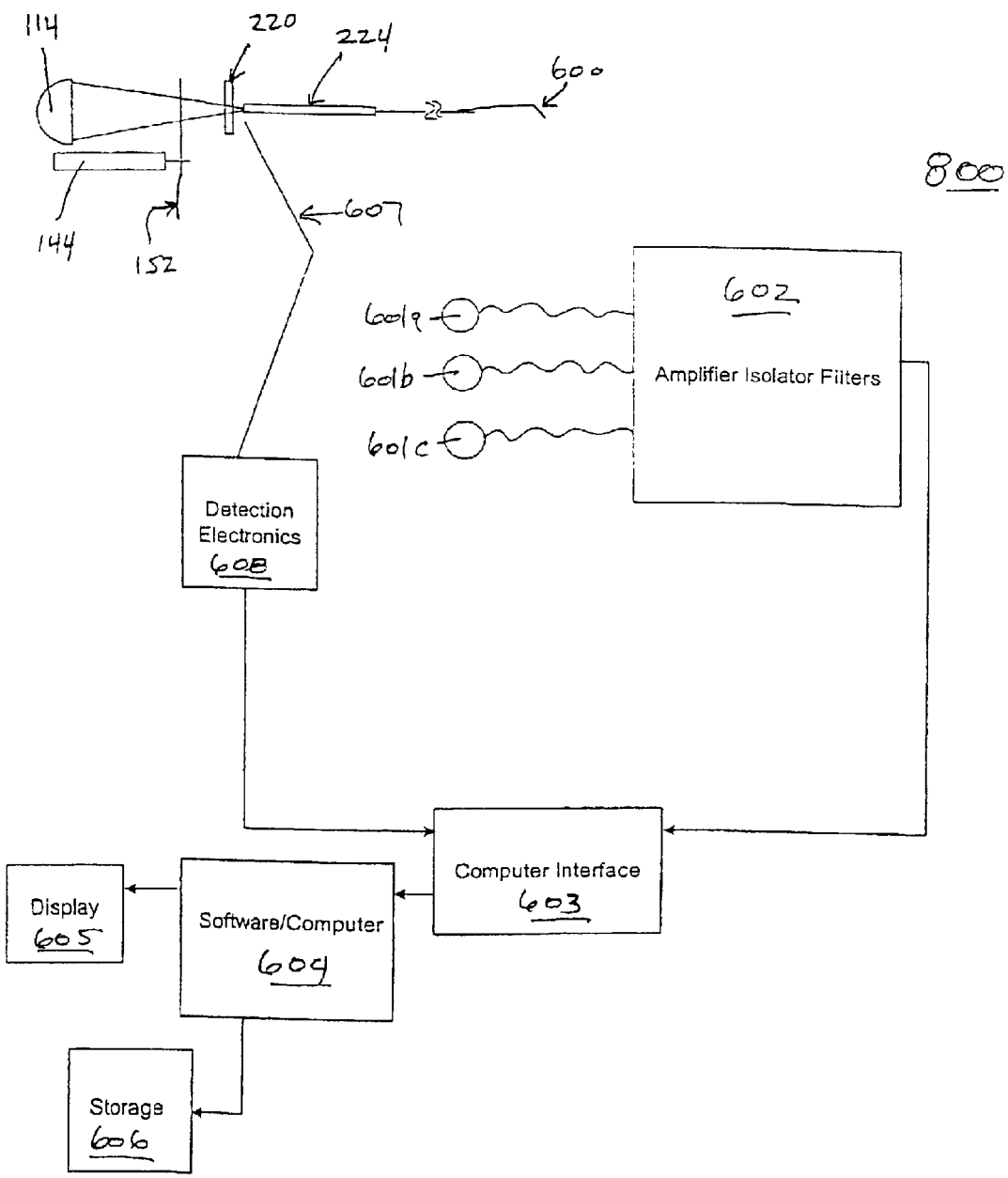
FIG. 8 depicts a system for monitoring and analyzing signals generated to an illuminator of this invention and physiological signals produced in response to signals generated by the illuminator.

For many applications, it is desirable to provide software and a computer with a reference signal to which information coming back from sensors placed on the skin can be compared to the desired output beam. An embodiment 800 of such a system for controlling illuminator function is depicted in FIG. 8. FIG. 8 depicts lamp 114, interrupter motor 144, and the interrupter disk 152, which interrupts the beam of radiation going through filter 220, and entering fiber optic cable 224. The fiber optic cable 224 can be any of the types described herein. The end effector 600 can also be of any type. To make comparisons of output radiation and the desired response, an aspect of this system is the ability to interrupt the output signal at a known frequency and/or divert a portion of that signal to the computer for analysis. A portion of the signal can be detected by a pick-off 607. Fiber optic signal pick-off 607 and detection electronics 608, can condition the signal for entry into the computer interface 603. Other means of detecting the signal are possible such as discrete pick-off from the fiber optic cable itself or from monitoring the position of the interrupter and computing the beginning and ending of the radiation going down the fiber optic cable. The position of illumination apertures 204 may be determined by an encoder instead of a pick-off.

One desirable feature of the system, whether the pick-off is achieved by software or by hardware, can include providing the software in the computer with a reference signal by which information coming back from sensors placed on the target (e.g., skin) at selected sites can be compared to the reference output signal generated by the illuminator and captured by the signal pick-off 607. For therapeutic uses, detectors 601a, 601b and 601c can be sEMG detectors, thermal sensors, muscle probe detectors, or any other type of biological or physiological sensor. The signal from the sensors 601a, 601b and 601c passes through amplifier assembly 602 comprising an amplifier, isolator and optionally, filters which are designed to augment the signal of interest which will be compared to a reference signal. The amplifier filter assembly 602 can be commercially obtained from a variety of vendors.

One purpose of the amplifier assembly is to allow a human subject to have sensors placed on them without the risk of electrical signals from the computer interface from causing harm to the subject. It can be desirable that the amplifier assembly be able to pass signals having frequencies up to around 600 Hz and optionally, it maybe desirable to provide a filter for reducing ambient noise, by way of illustration only, 50/60 Hz noise. Alternatively, one can provide filters to reduce any signal that is not desired, by way of example only, EEG signals, EMG signals, and the like, thereby permitting one to more easily detect and analyze signals that represent a desired response. Alternatively, this filtration may take place later using software-configured filters. The output of the amplifier isolator 602 may be an analog signal going to an analog interface and then to the computer 603, or it may be converted to digital signals and then routed to the computer 603. The software and the computer 604, can desirably perform analyses of the signals, including joint time and frequency analysis, or other types of analyses. It can be desirable to place the sensors at locations where the maximum physiological effects are to be observed. For example, for monitoring therapeutics of nerves, it can be desirable to place sensors at locations of maximum innervation of the muscle of interest. Alternatively, to monitor muscle activity, sEMG electrodes can be desirably placed near the muscle to be studied and treated. Multiple sensors can be used to determine the amount of signal which is coming through at various points on the body.

Placement of the illuminator's end effectors can be selected to provide signals from the output radiation beam into the nervous system of the individual being studied. The software desirably can permit the operator to determine the percentage of signal that is arriving at the various sensors, and thus, maybe an indication of therapeutic effectiveness. The software can use the pulsed input signal and the frequency of that signal to discriminate information returning from the sensors which have a phase and time relationship to the input signal. The system can thus be operated in a fashion similar to that of a nerve conduction velocity study carried out using electrical stimulation. However, rather than electrical stimulation, systems of this invention can use electromagnetic radiation provided at selected intensities, pulse durations and pulse frequencies. In those embodiments using a rotating interrupter, the interrupter's rotational velocity can determine the pulse frequency. The pulse duration can be selected by adjusting the size of the interrupter's slit relative to the circumference and rotational velocity of the interrupter disk. In embodiments using electrical or other means to provide pulses, the input can be in the form of control signals to the interrupter. Different variables, including pulse duration, frequency, and intensity can be independently controlled.

The combination of the wavelength, bandwidth, pulse duration and pulse frequency can affect selected excitable tissues, depending on intrinsic responsiveness of those tissues to the radiation. The relationships of output signals from tissues to the input signals can be determined for a variety of different wavelengths and frequencies. In certain embodiments, these determinations can be made automatically with the aid of a computer system that had been pre-programmed for the purpose. The ability to make measurements at a variety of different wavelengths and frequencies of intermittent radiation or signal can permit the adjustment of illuminators to maximize outputs detected by the sensors. The combination of multiple illumination systems, multiple end effectors and/or multiple interrupters can permit the practitioner to more finely select desired variables to optimize diagnosis and treatment of disorders of excitable tissues, such as nerves, muscles and connective tissues.

The illumination system may be replaced by electronic emitting device, such as LED, once the selected wavelengths are known and the ability to scan wavelengths provides the operator with additional control. The system allows the ability to go and determine the nerve conduction properties of an individual before and after treatment in order to determine if nerve conduction has improved. In one specific application for persons with diabetic neuropathy of the feet, the detection of nerve conduction may be used in conjunction with other standard techniques for monitoring the abilities of the patient such as monofilament testing. The ability to inject signals and vary both the frequency and the wavelengths permits the operator/system to determine the optimal conditions for treating this and other disorders.

In certain embodiments, optical systems other than waveguides can be used to transmit the radiation and resize or reconfigure a radiation beam as required by some other piece of equipment.

Example 8

Alternative Optical Configuration I

Figure 9:
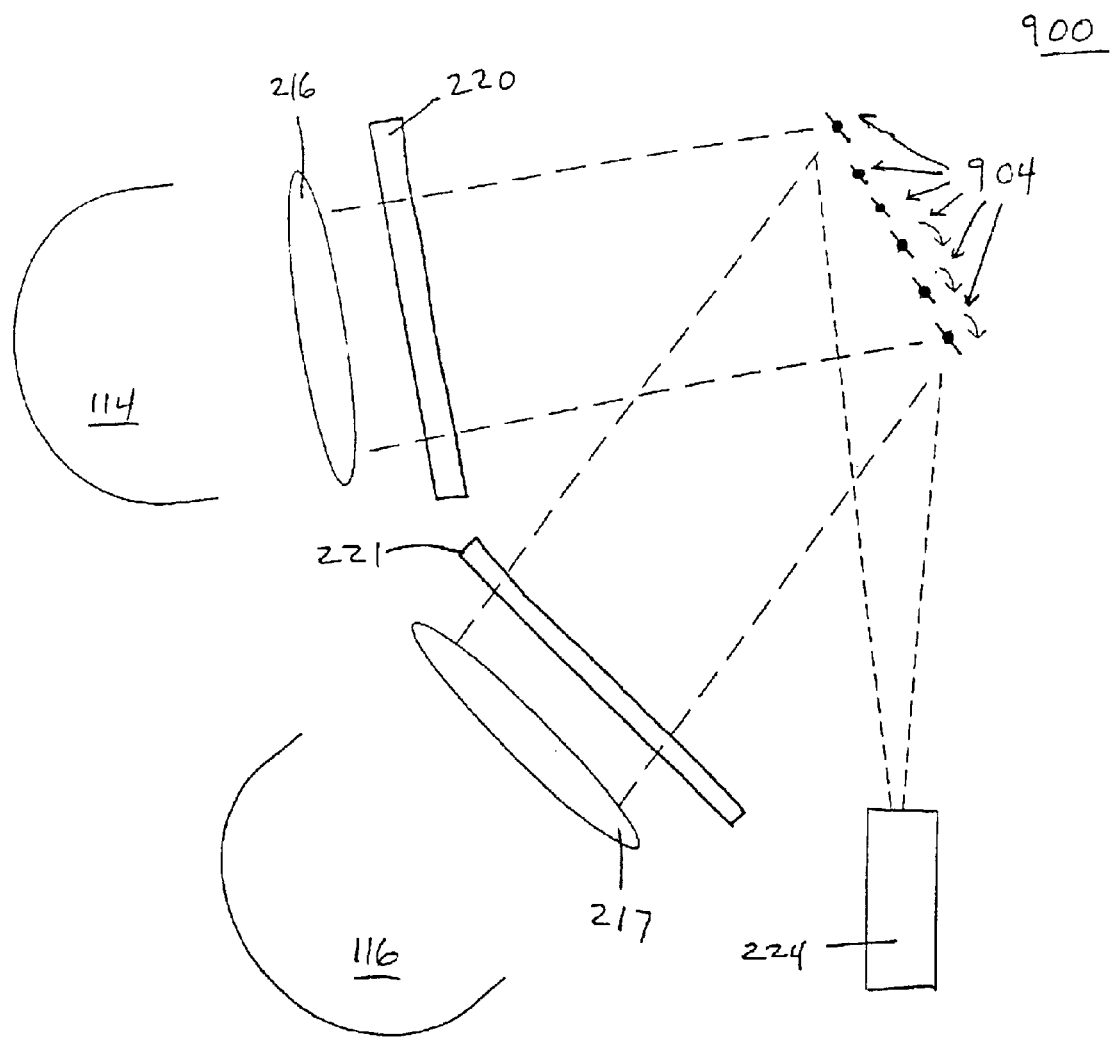
FIG. 9 depicts an embodiment of this invention in which output of two radiation sources is combined into a single output beam.

In certain of these embodiments, mirror beam selectors can be provided to direct certain portions of emitted radiation. FIG. 9 depicts an alternative embodiment 900 of this invention in which two beams of radiation are combined into a single output beam. Lamps 114 and 116 produce electromagnetic radiation that passes through lenses 216 and 217 and then through filter arrays 220 and 221. The beams of radiation are then reflected by rotatable mirrors 904. A portion of the reflected radiation then is captured by waveguide 224 for remote transmission to a site of illumination. It can be appreciated that by rotating the mirrors selectively, selected portions of the radiation from either source can be reflected to waveguide 224.

Example 9

Alternative Optical Configuration II

Figure 10:
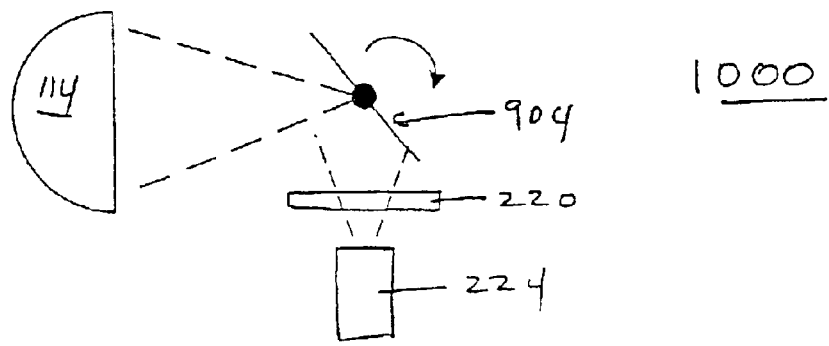
FIG. 10 depicts a portion of an embodiment of this invention having a rotating mirror to interrupt an output beam.

Another embodiment 1000 is depicted in FIG. 10. Lamp 114 produces a beam of electromagnetic radiation, a portion of which is reflected from rotatable mirror 904, passes through filter 224 and is captured by waveguide 224.

Example 10

Alternative Optical Configuration III

Figure 11:
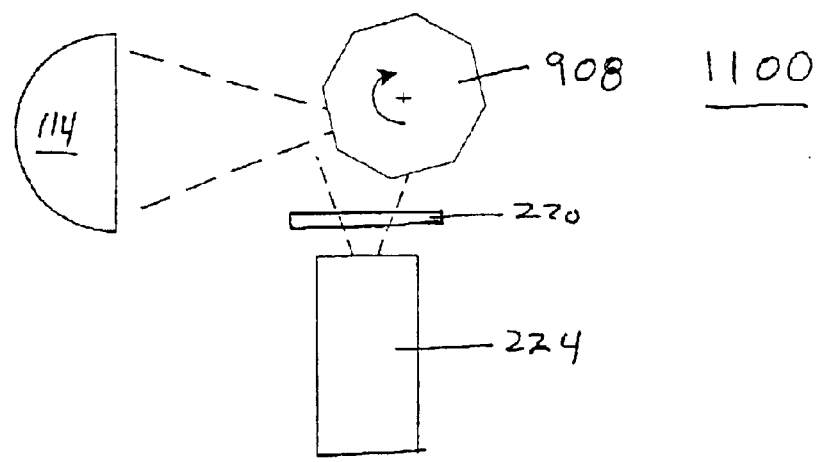
FIG. 11 depicts an alternative portion of an embodiment of this invention having a rotating, multifaceted mirror.

Another embodiment 1100 of this invention is depicted in FIG. 11. Lamp 114 produces a beam of radiation that is reflected by multifaceted rotatable mirror 908. A portion of the reflected beam passes through filter 220 and is then captured by waveguide 224.

Example 11

Alternative Optical Configuration IV

Figure 12:
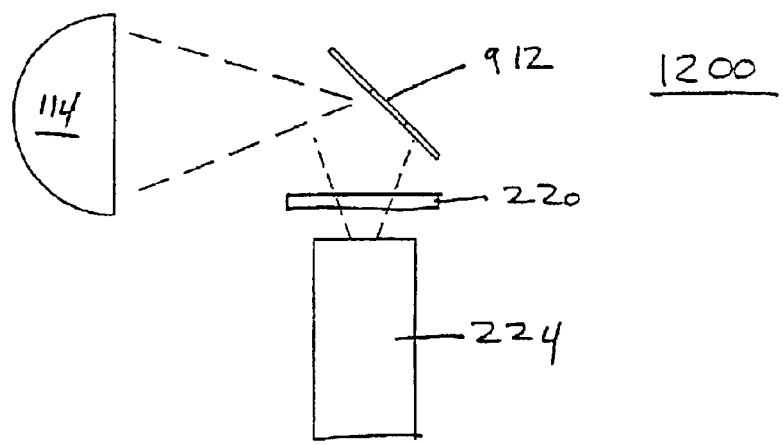
FIG. 12 depicts a portion of an embodiment of this invention having a multiple segment mirror.

In another embodiment of this invention 1200 depicted in FIG. 12. Lamp 114 produces a beam of electromagnetic radiation that is reflected by a multiple segment mirror 912. Mirror 912 can be, for example, a DLP™ mirror.

Example 12

Alternative Optical Configuration V

Figure 13:
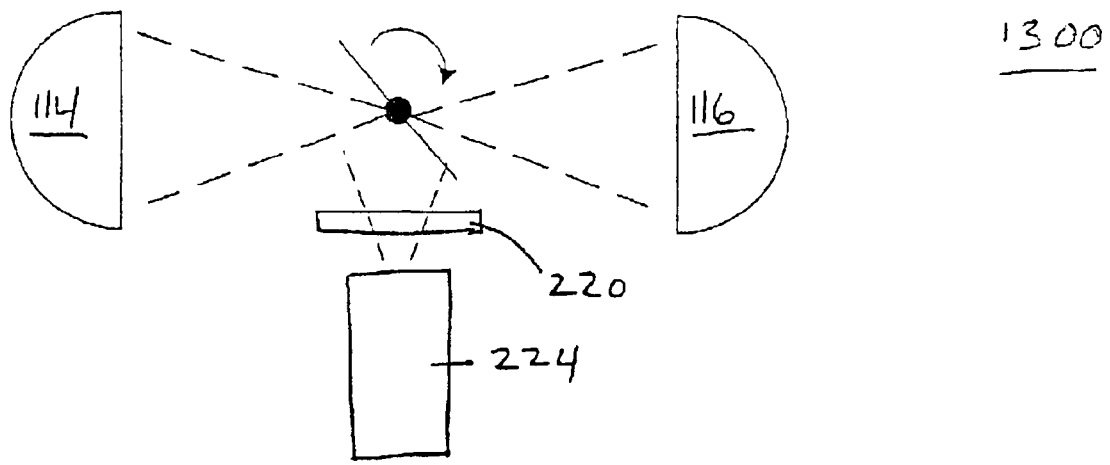
FIG. 13 depicts a portion of an embodiment of this invention having a rotatable mirror and two sources of electromagnetic radiation.

In yet another embodiment of this invention 1300 depicted in FIG. 13, a beam can be selected from between two different lamps 114 and 116. As rotating mirror 904 rotates, the beams of radiation arising from the lamps 114 and 116, respectively, can be reflected alternatively through filter 220 and captured by waveguide 224.

Example 13

Alternative Optical Configuration VI

Figure 14:
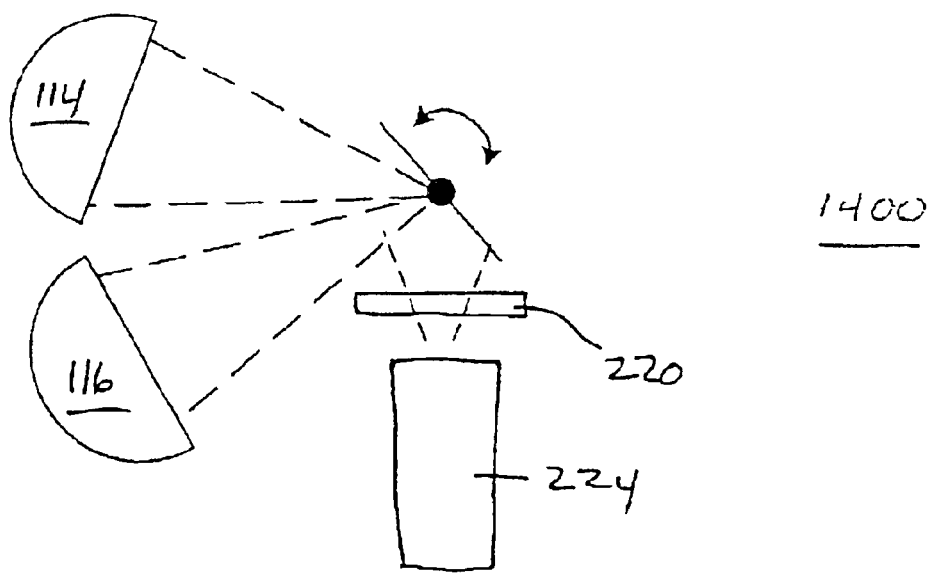
FIG. 14 depicts an alternative portion of an embodiment of this invention having a rotatable mirror and two sources of electromagnetic radiation.

In a further embodiment of this invention 1400 depicted in FIG. 14, lamps 114 and 116 are shown near each other. As rotating mirror 904 rotates, the beams of radiation produced by lamps 114 and 116, respectively, can be reflected alternatively through filter 220 and captured by waveguide 224.

Example 14

Selecting Bandwidth Using a Circular Filter

Figure 15A:
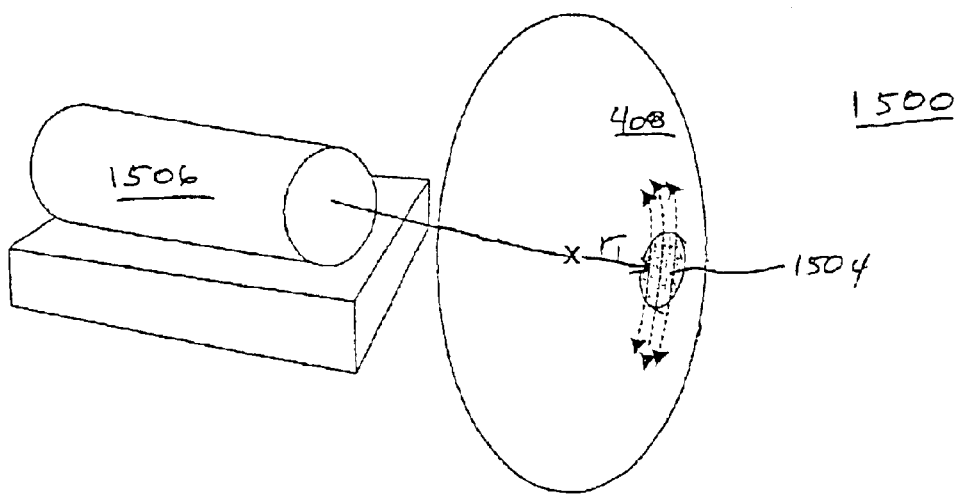
FIGS. 15a and 15b depict an embodiment of this invention having a circular filter array.
Figure 15B:
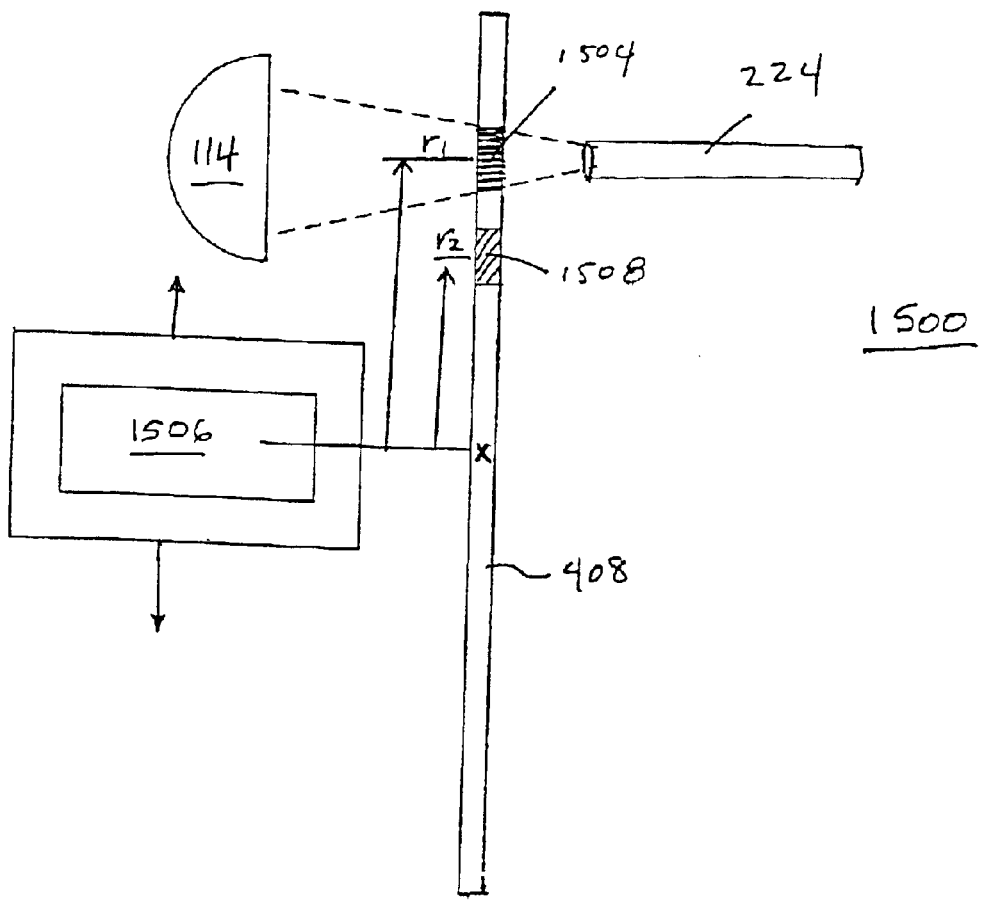

FIGS. 15a and 15b depict an embodiment 1500 of this invention in which the bandwidth of a beam of radiation is selected using a circular filter 408. FIG. 15a depicts circular filter 408 that is rotated by motor 1506 about an axis of rotation x. Filter 408 has area 1504 which has one bandwidth that is at radius r from axis x.

FIG. 15b depicts a side view of the embodiment 1500, in which lamp 114 is shown producing a beam of radiation that passes through area 1504 of filter 408 and then is captured by waveguide 224. Area 1504 is shown at radius r1 relative to the axis of rotation x. To change the bandwidth of the beam of radiation captured by waveguide 224, motor 1506 moves in response to forces produced by another motor (not shown), which can translate motor assembly 1506 (arrows) relative to the lamp 114, so that area 1508 (at radius r2) from axis x on filter 408 is now in position relative to lamp 114, so that the radiation passing through area 1508 can be captured by waveguide 224.

Example 15

Selection of Bandwidth by Variable Aperture

Figure 16A:
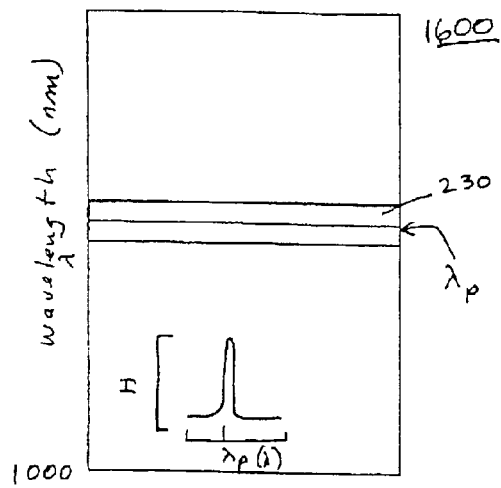
FIGS. 16a–16c depict embodiments of this invention having apertures that control the peak wavelength and bandwidth of a beam of radiation passing through a filter array.
Figure 16B:
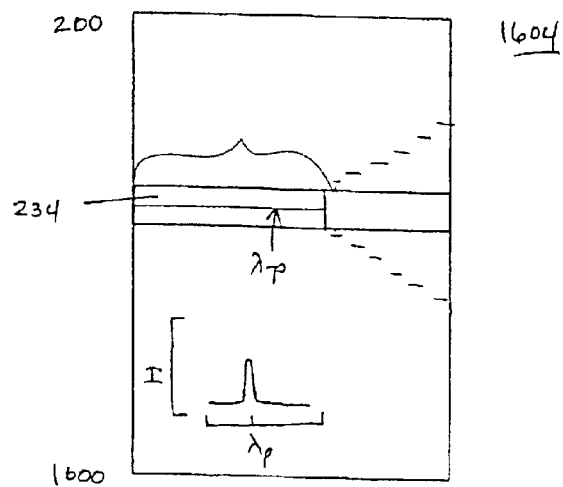
Figure 16C:
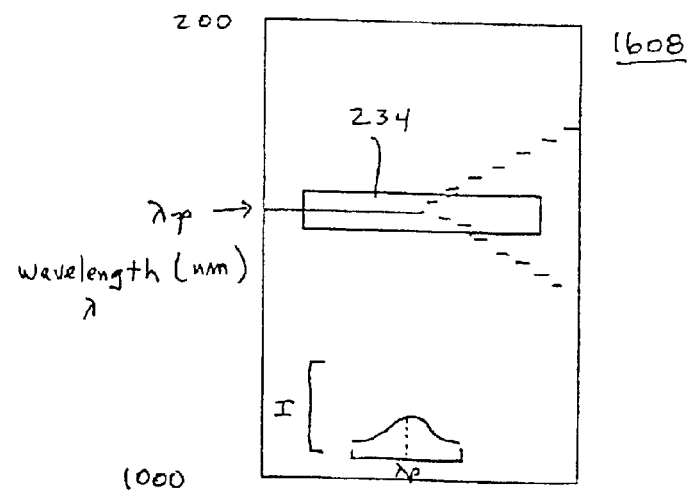

In certain embodiments of this invention, the bandpass characteristics can be selected by adjusting an aperture. FIGS. 16a–16c depict such embodiments. FIG. 16a depicts an embodiment 1600 in which aperture 230 overlays a filter array 1601. The peak wavelength λp is shown, as is the spectrum of intensity I at each wavelength λ (insert). The maximum intensity is found at λp.

FIG. 16b depicts an embodiment 1604 in which filter array 1602 has an area of narrow bandwidth filters (left side), and an area of progressively wider bandwidth filters (right side). The position of λp is shown as in FIG. 16a. Aperture 234 is shown over the narrow bandwidth area of filter 1602, so the spectrum (insert) shows a maximum wavelength at λp, as in FIG. 16a, but the intensity I is less than that for FIG. 16a, reflecting the decreased area of filter 1602 through which the output beam passes.

FIG. 16c depicts an embodiment 1608 in which filter 1602 and aperture 234 are as shown in FIG. 16b except that aperture 234 is displaced to the right compared to FIG. 16b. By being displaced into the area of wider bandwidth, the spectrum of output radiation (insert) shows a peak at λp, but also has a wider bandwidth than depicted in FIG. 16b. In other embodiments, aperture 234 can be expandable in either the horizontal or the vertical dimension, or both. For example, by expanding the horizontal dimension of aperture 234 to the right, one can include broader bandwidths and keep the intensity of λp the same. Thus by controlling the left and/or right sides of aperture 234, one can control the λp as well as the bandwidth and the relative intensities of the different wavelengths transmitted.

Example 16

Selection of Bandwidth by Liquid Crystal Shutters

Figure 17:
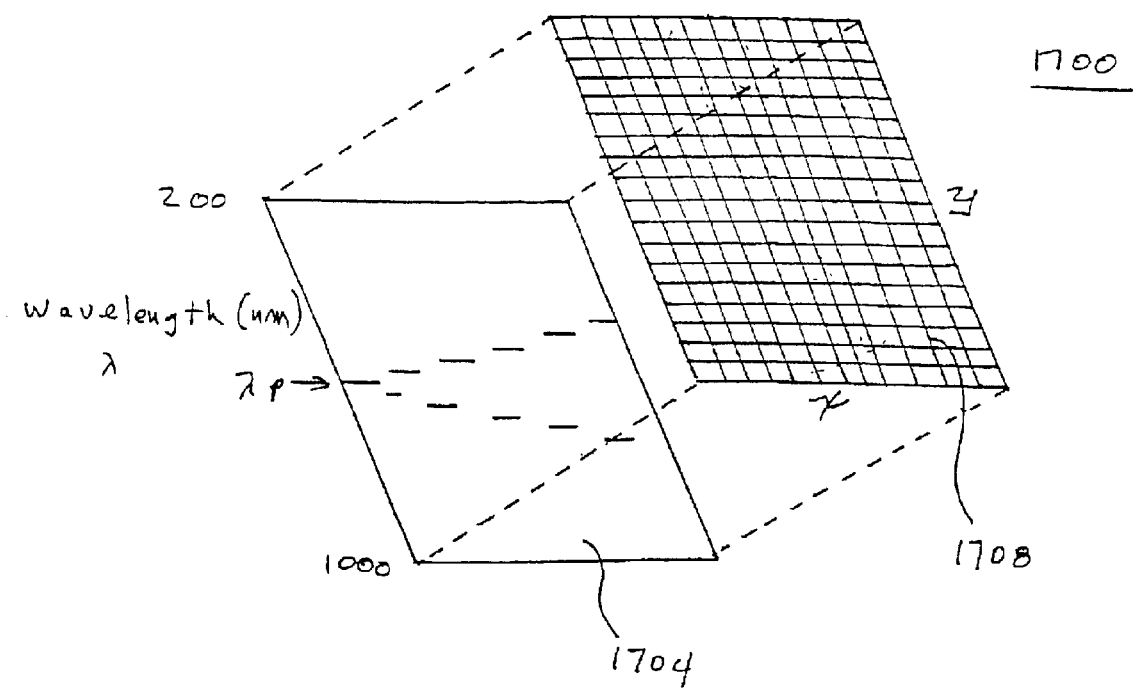
FIG. 17 depicts an embodiment of this invention in which a shutter array is used to select peak wavelength and bandwidth of an output beam of electromagnetic radiation.

FIG. 17 depicts an embodiment 1700 of this invention in which filter array 1704 has areas of different bandwidth filters thereon. On the left side of filter array 1704, λp is shown, and progressively to the right, areas of progressively wider bandwidth are present (with λp shown as horizontal lines). An array of liquid crystal shutters 1708 is shown in relationship to filter array 1704. Shutter array 1708 has two dimensions, x and y, so each shutter element in the two-dimensional shutter array 1708 has a unique x and y coordinate. The horizontal x dimension has elements addressed by a, b, c, d, e, and so on. The vertical y dimension has elements addressed by 1, 2, 3, 4, 5 and so on. Each element can be controlled by a voltage applied to that element, so that in one voltage state, the liquid crystal of that element is "open" and radiation can pass through that element. Thus, to select a bandwidth in this embodiment, one can select those x and y coordinates that will open the desired pattern of shutters. It can be readily appreciated that shutter array 1708 can be effectively used to select desired λp and bandwidths from a filter array that is not offset as in filter array 1704. In fact, because embodiment 1700 has no moving mechanical parts, one can select and rapidly change selection of λp and bandwidth as desired for that particular application.

Example 17

Selection of Peak Wavelength and Bandwidth by Liquid Crystal Shutters

Figure 18:
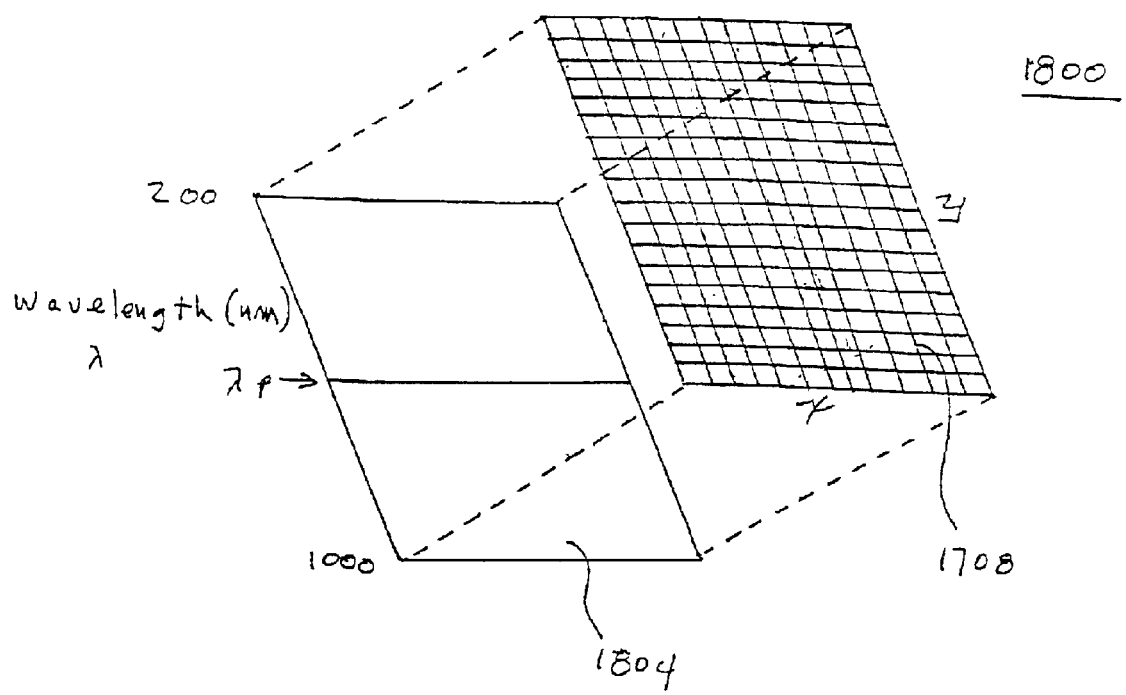
FIG. 18 depicts an embodiment of this invention in which a shutter array is used to select peak wavelength, bandwidth, and intensity of an output beam of electromagnetic radiation.

FIG. 18 depicts an embodiment 1800 of this invention in which filter array 1804 is a single array of filter elements and a desired peak wavelength λp, that is in the same location across the horizontal direction of filter array 1804. The vertical direction of filter array 1804 depicts different wavelengths. As with FIG. 17, an array of liquid crystal shutters 1708 ("shutter array") is depicted in relationship to filter array 1804. In this embodiment 1800, λp is selected by opening up the shutters immediately above the portion of filter array 1804 that corresponds to λp. To increase the intensity of the output beam, additional shutters in the horizontal, or x direction can be opened, thereby permitting additional radiation to pass through the shutter array. Opening additional shutters in the x dimension can increase the intensity further, until all of the shutters are opened.

To select a bandwidth, one can open shutters in the y dimension different from the location immediately corresponding to λp. To increase the bandwidth, one can open additional shutters in the y dimension from λp. Using this type of embodiment, one can produce an output beam having any λp and any bandwidth that are permitted by the range of wavelengths incorporated into filter array 1804. Thus, to provide a beam having greatest intensity at λp, one can open more shutters in the x dimension of shutter array 1708 corresponding to λp than shutters at any other wavelength.

In certain embodiments, one can produce an output beam having a plurality of λp by opening more shutters at each of two selected wavelengths than at other wavelengths. If desired, the relative intensity at the two peak wavelengths can be the same or can be different. Thus, using a shutter array as described in Examples 16 and 17, one can select between a variety of different output beams. One can select a beam having the output of a single filter element λp, at a number of different intensities depending on the output of the lamp and the number of open shutters at λp. Alternatively, one can select an output beam having λp and a bandwidth that depends on shutters at different wavelengths. Moreover, one can select a bandwidth pattern wherein the intensity of the output beam can be selected by opening up different patterns of shutters. Because individual elements of the shutter array 1708 can be controlled rapidly using electronic signals addressed by x and y coordinates, these embodiments can provide a high degree of flexibility and control over the wavelengths in the output beam.

Example 18

Diode Array Illuminator

In other embodiments, illuminators are provide that comprise a variety of diode emitters, selected to provide a variety of different output wavelengths. By selecting which of such emitters are activated, the central wavelength, bandpass, wavelength variation, frequency, intensity and pulse duration can be regulated. If desired, a computer system can be used along with a series of diode emitters to provide preset control over the different variables.

Example 19

Interrupter Designs

Figure 19:
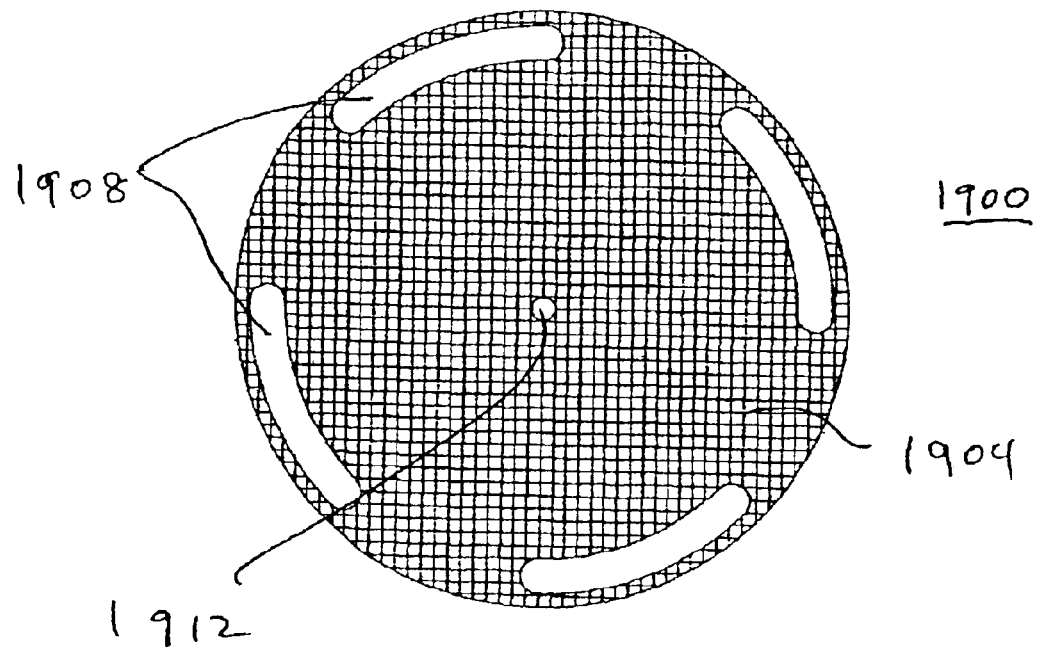
FIG. 19 depicts part of an embodiment of this invention, comprising an interrupter wheel having regularly spaced transparent portions to permit light to pass through therethrough. The duty cycle is fixed.

In certain embodiments of this invention, interrupters are provided to permit production of electromagnetic radiation having desired patterns. FIG. 19 depicts an embodiment of this invention in which an interrupter 1900 has a disk portion 1904, 4 transparent areas 1908. and an axis of rotation 1912. Interrupter 1900 is placed in front of a beam of electromagnetic radiation (not shown) and the beam is interrupted when an opaque portion of disk 1904 blocks the radiation. When a transparent portion 1908 passes in front of the beam, radiation can pass through the interrupter and can be directed toward an object for illumination.

Figure 20:
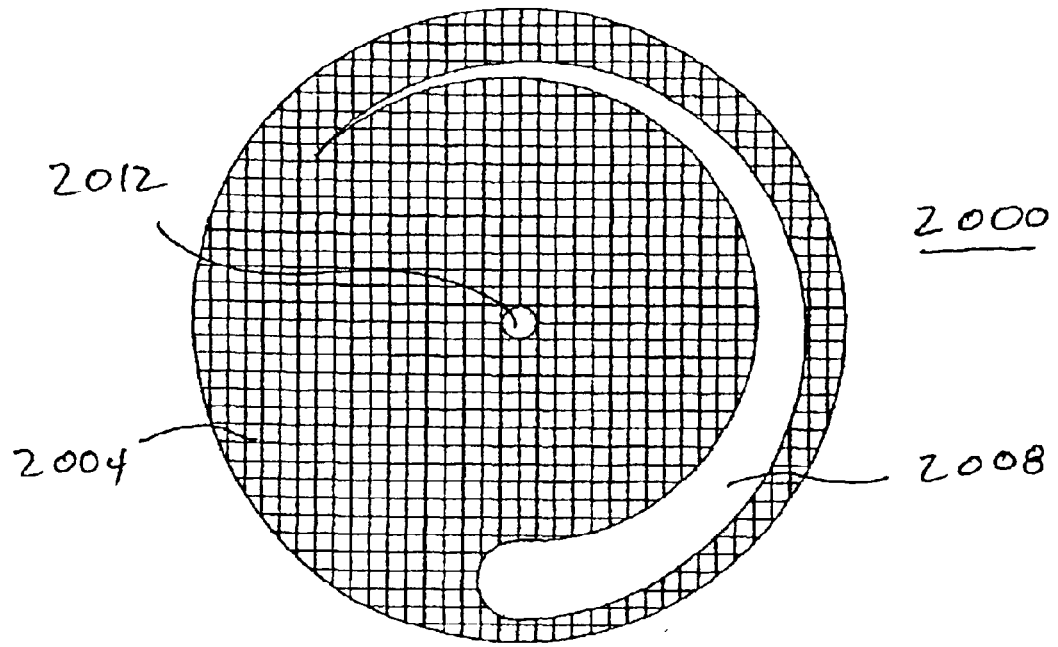
FIG. 20 depicts an alternative part of an embodiment of this invention, in which an interrupter wheel has a transparent portion to permit a linear change in light intensity.

FIG. 20 depicts an embodiment of an interrupter of this invention 2000, having a disk portion 2004 a transparent portion 2008 and an axis of rotation 2012. Upon rotation of interrupter 2000, when electromagnetic radiation passes through the narrowest portion of transparent portion 2008, the intensity of radiation can be minimized. When used in conjunction with a linear array of filters as described herein, the transparent portion 2008 can be used to adjust the wavelength bandpass. Upon rotation of the interrupter so that a wider portion of the transparent portion 2008 is in front of the beam of radiation, more radiation or a wider bandpass of radiation can pass through.

Figure 21:
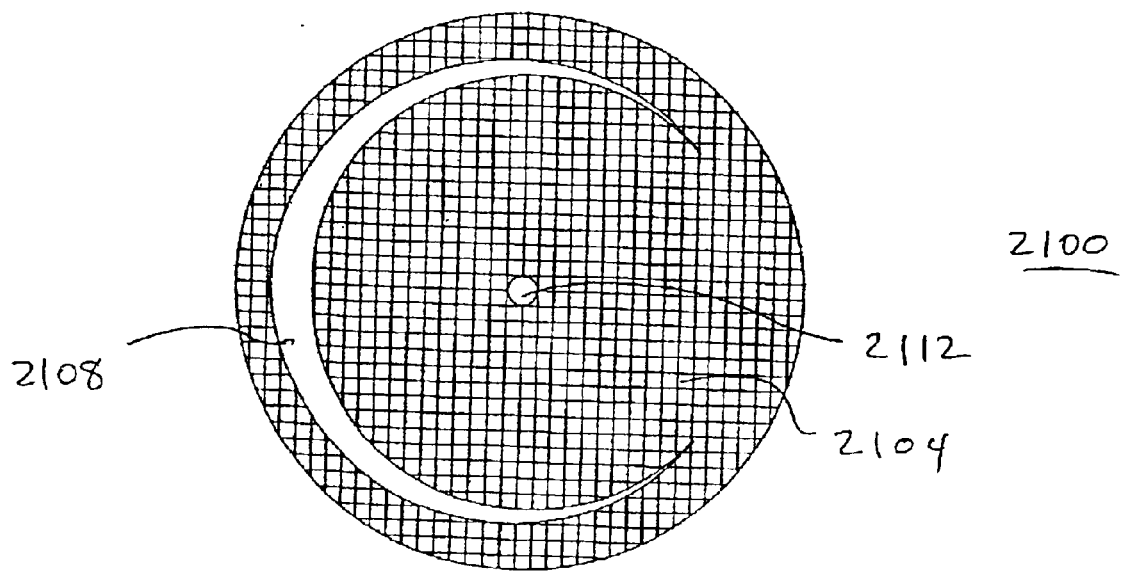
FIG. 21 depicts an alternative part of an embodiment of this invention, in which an interrupter wheel has a transparent portion to permit both increase and decrease in light intensity passing through the wheel.

FIG. 21 depicts another embodiment of an interrupter of this invention 2100, having a disk portion 2104, a transparent portion 2108, and an axis of rotation 2112. Upon rotation of interrupter 2100, light passing from a narrow end to a wider portion of 2108 can result in passage of a beam having higher intensity and/or wider wavelength bandpass. As the transparent portion 2108 continues further, the beam can be progressively occluded by the narrowing portion of 2108 and thereby the intensity and/or wavelength bandpass can decrease.

Figure 22:
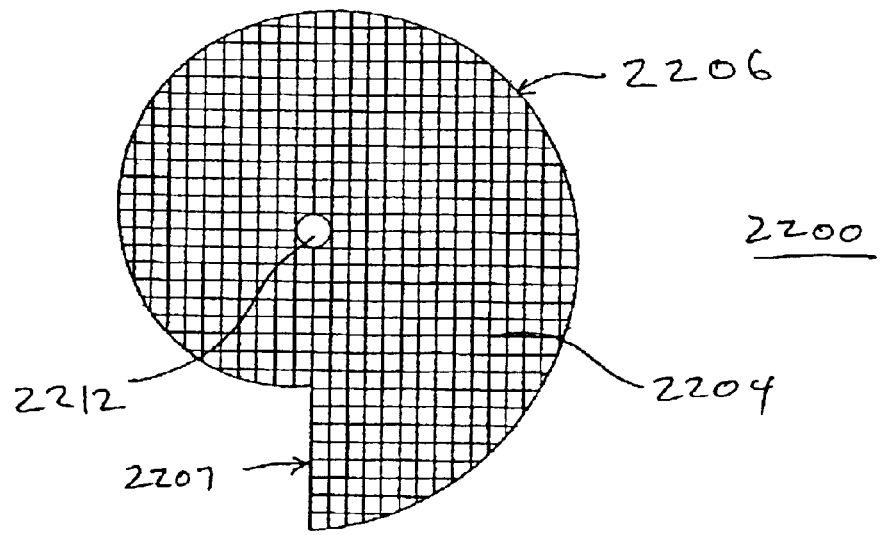
FIG. 22 depicts an alternative part of an embodiment of this invention, in which an interrupter wheel has an acircular edge, so that with rotation, the beam of light can be at least partially occluded.

FIG. 22 depicts a yet further embodiment of an interrupter of this invention 2200, having a disk portion 2204 a spiral edge 2206 and an axis of rotation 2212. Upon rotation of interrupter 2200, a portion of a beam of electromagnetic radiation (not shown) can be occluded by edge 2206. Further rotation can cause greater occlusion of the beam, thereby decreasing intensity and/or wavelength bandpass. When the interrupter 2200 rotates sufficiently so that the beam passes by radial edge 2207, the intensity and/or wavelength bandpass can abruptly change.

Figure 23:
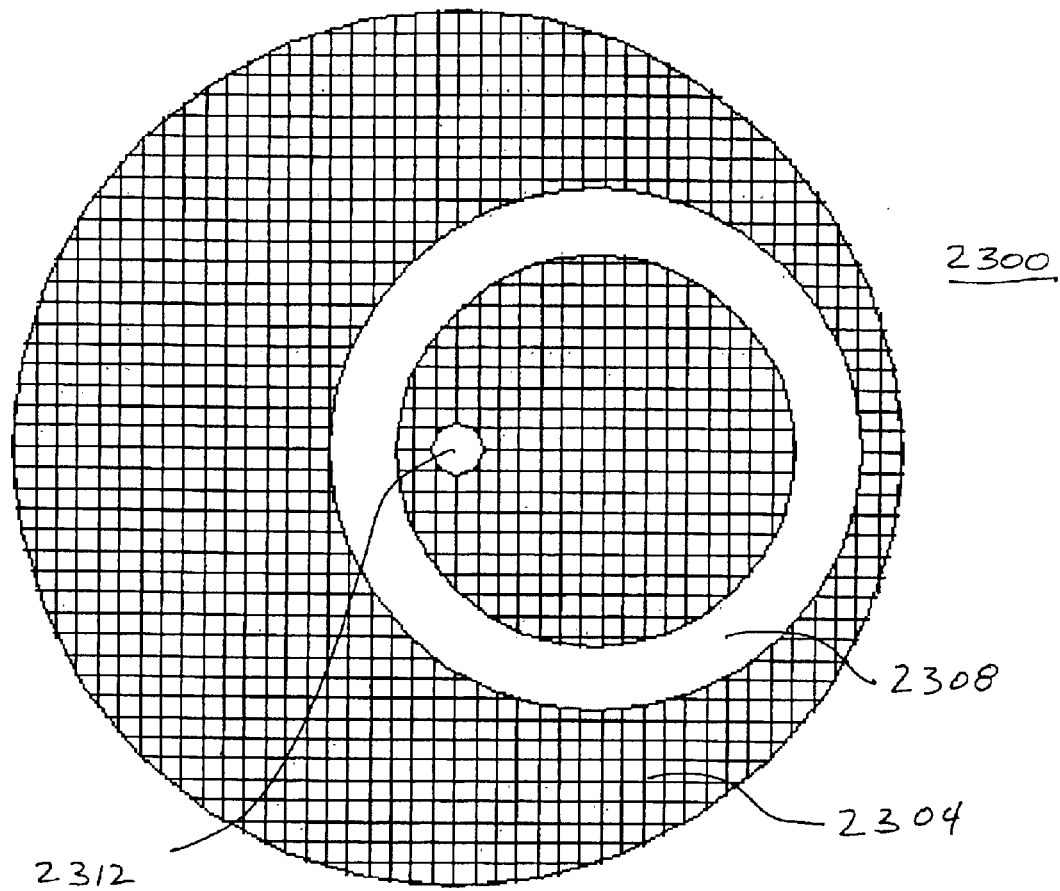
FIG. 23 depicts an alternative part of an embodiment of this invention, in which an interrupter wheel has an eccentric transparent portion.

FIG. 23 depicts a further embodiment of an interrupter of this invention 2300 having a disk portion 2304, an eccentric window or transparent portion 2308 and an axis of rotation 2312. Upon rotation of interrupter 2300, the transparent portion 2308 rotates with respect to an underlying linear filter array (not shown), thereby exposing different parts of the filter array with each revolution of interrupter 2300. By exposing different parts of the filter array, the wavelength of radiation passing through transparent portion 2308 can vary over time.

The above examples and descriptions are by way of illustration only, and are not intended to be limiting to the scope of the invention. Other devices and systems embodying features of this invention can be contemplated, and all of those devices and systems are considered to be part of this invention.

Industrial Applicability

Illuminators and systems for providing electromagnetic radiation are useful for therapeutic applications involving exposure of subjects to radiation of selected wavelength, bandwidth, pulse frequency and pulse duration. The illuminators and systems are also useful for applications in machine vision, grading material characteristics, microscope illumination, catalysis in radiation-triggered chemical reactions, testing of optical assemblies and determining dispersion characteristics of materials. Computer control systems permit the acquisition and analysis of physiological and other information relating to the effects of illumination.

We Claim:

1. An illuminator for providing an output beam of electromagnetic radiation, comprising:
   a source of electromagnetic radiation;
   at least two filter arrays comprising filter elements, each filter element having a peak wavelength, and wherein said filter arrays are non-overlapping so that each wavelength maximum is offset relative to each of said other arrays, forming a track, wherein said filter arrays comprise a plurality of concentric circular filter arras;
   an aperture adapted for selecting at least one of peak wavelength, bandwidth and intensity, said aperture positioned relative to said at least two filter arrays, so an output beam is formed; and
   a waveguide associated with said output beam.

2. The illuminator of claim 1, further comprising at least one of the group consisting of a lens and a heat filter.

3. The illuminator of claim 1, further comprising a detector for monitoring a physiological response to said illumination.

4. The illuminator of claim 1, further comprising a calibration source of electromagnetic radiation.

5. The illuminator of claim 1, further comprising a signal pickoff.

6. The illuminator of claim 1, further comprising an information storage device coupled to a computer.

7. The illuminator of claim 1, wherein said output beams have a peak wavelength in the range of ultraviolet to infrared wavelengths.

8. The illuminator of claim 1, further comprising at least one interrupter.

9. The illuminator of claim 1, wherein at least one of said waveguides comprises an optical fiber.

10. The illuminator of claim 1, wherein output beam has a shape selected from the group consisting of circular, rectangular, triangular, annular and linear.

11. The illuminator of claim 1, wherein said source is selected from the group consisting of incandescent, gas discharge and radiation emitting diode devices.

12. The illuminator of claim 1, comprising a first track having no wavelength offsets and a plurality of additional, non-overlapping tracks, each of said non-overlapping tracks having an offset different from the offset of each of said other tracks.

13. The illuminator of claim 12, wherein the offsets of each of said non-overlapping tracks are laterally positioned, and said offsets increase progressively with lateral distance from said track having no offset.

14. The illuminator of claim 1, comprising at least two apertures.

15. The illuminator of claim 14, wherein said apertures are selected from the group consisting of mechanical shutters, mirrors and electro-optical shutters.

16. The illuminator of claim 1, further comprising a computer interface for receiving input signals and for providing output signals to at least one of a brightness control for a source of electromagnetic radiation, a wavelength driver, and a bandwidth driver.

17. The illuminator of claim 16, further comprising:
   a controller of at least one of pulse width and pulse duration; and
   means for providing illumination in pulses of selected duration and frequency.

18. The illuminator of claim 17, wherein said means for providing illumination in pulses is selected from the group consisting of mechanical choppers, electro-optical shutters and mechanical shutters.

19. An illuminator for providing a plurality of output beams of electromagnetic radiation, comprising:
   a source providing at least two beams of electromagnetic radiation;
   at least two filter arrays comprising filter elements, each filter element having a peak wavelength, and
   wherein said filter arrays are non-overlapping so that each wavelength maximum is offset relative to each of said other arrays, forming a track, wherein said filter arrays comprise a plurality of concentric circular filter arrays;
   an aperture adapted for selecting at least one of peak wavelength, bandwidth and intensity, said aperture positioned relative to said at least two filter arrays, so at least two output beams are formed; and
   a waveguide associated with at least one of said output beams.

20. The illuminator of claim 19, wherein at least one variable of each of said plurality of output beams is separately controllable relative to another output beam.

21. The illuminator of claim 19, further comprising means for interrupting at least one of said output beams.

22. The illuminator of claim 21, wherein said interrupter is selected from the group consisting of mechanical choppers, mirrors, mechanical shutters and electro-optical shutters.

* * * * *

UNITED STATES PATENT AND TRADEMARK OFFICE
CERTIFICATE OF CORRECTION

PATENT NO. : 6,886,964 B2  Page 1 of 1
APPLICATION NO. : 10/180643
DATED : May 3, 2005
INVENTOR(S) : Gardiner et al.

It is certified that error appears in the above-identified patent and that said Letters Patent is hereby corrected as shown below:

Col. 33, line 47, after "filter" delete "arras" and insert --arrays--

Signed and Sealed this

Fourteenth Day of August, 2007

JON W. DUDAS
*Director of the United States Patent and Trademark Office*